United States Patent
Heinrich et al.

(10) Patent No.: US 9,238,651 B2
(45) Date of Patent: *Jan. 19, 2016

(54) 1-H-PYRROLO[2,3-B]PYRIDINE DERIVATIVES

(71) Applicant: Merck Patent GmbH, Darmstadt (DE)

(72) Inventors: Timo Heinrich, Gross-Umstadt (DE); Margarita Wucherer-Plietker, Messel (DE); Hans-Peter Buchstaller, Griesheim (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/458,759

(22) Filed: Aug. 13, 2014

(65) Prior Publication Data

US 2014/0371215 A1 Dec. 18, 2014

Related U.S. Application Data

(60) Continuation of application No. 14/044,330, filed on Oct. 2, 2013, now Pat. No. 8,895,575, which is a division of application No. 13/883,411, filed as application No. PCT/EP2011/005127 on Oct. 12, 2011, now Pat. No. 8,664,236.

(30) Foreign Application Priority Data

Nov. 5, 2010 (DE) .......................... 10 2010 050 558

(51) Int. Cl.
| | | |
|---|---|---|
| *A61K 31/538* | (2006.01) | |
| *C07D 471/04* | (2006.01) | |
| *A61K 31/506* | (2006.01) | |
| *A61K 31/5377* | (2006.01) | |
| *A61K 45/06* | (2006.01) | |
| *A61N 5/10* | (2006.01) | |

(52) U.S. Cl.
CPC ............ *C07D 471/04* (2013.01); *A61K 31/506* (2013.01); *A61K 31/538* (2013.01); *A61K 31/5377* (2013.01); *A61K 45/06* (2013.01); *A61N 5/10* (2013.01)

(58) Field of Classification Search
CPC ... A61K 31/506; A61K 31/538; A61K 45/06; A61K 31/5377; C07D 471/04
See application file for complete search history.

(56) References Cited

U.S. PATENT DOCUMENTS

| 8,420,820 | B2 | 4/2013 | Wucherer-Plietker et al. |
| 8,664,236 | B2* | 3/2014 | Heinrich et al. .............. 514/275 |
| 8,895,575 | B2* | 11/2014 | Heinrich et al. .............. 514/275 |
| 2010/0137313 | A1 | 6/2010 | Boriack-Sjodin et al. |
| 2011/0218198 | A1 | 9/2011 | Wucherer-Plietker et al. |
| 2012/0270871 | A1 | 10/2012 | Wucherer-Plietker et al. |

FOREIGN PATENT DOCUMENTS

WO        2010000364 B1    1/2010

OTHER PUBLICATIONS

F. Bunz, Principles of Cancer Genetics 1-47, 1 (2008).*
P.K. Kuppen et al., 115 Histochemistry and Cell Biology, 67-72 (2001).*
J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*
S. Faderi et al., Myelodysplastic Syndromes, in 2 Cancer Principles & Practice of Oncology 2133 (V.T. DeVita, Jr. et al. eds., 7th ed., 2005).*
Kinase Inhibitors, Methods in Molecular Biology (B. Kuster ed., 2012).*
C. Peifer et al., 3 ChemMedChem, 1810-1838 (2008).*
A. Najafov et al., 433 Biochemical Journal, 357-369 (2011).*
B. Yang et al., 88 Journal of Neuroscience Research, 3090-3101 (2010).*
Raimondi et al., 18 Current Medicinal Chemistry, 2763-2769 (2011).*
International Search Report for PCT/EP2011/005127, Date of the actual completion of the international search: Nov. 25, 2011, Date of mailing of the international search report: Dec. 5, 2011.

* cited by examiner

*Primary Examiner* — Alexander R Pagano
(74) *Attorney, Agent, or Firm* — Millen White Zelano and Branigan, PC; John Sopp; Csaba Henter

(57) ABSTRACT

1H-Pyrrolo[2,3-b]pyridine compounds are inhibitors of cell proliferation/cell vitality and can be employed for the treatment of tumours.

20 Claims, No Drawings

1-H-PYRROLO[2,3-B]PYRIDINE DERIVATIVES

SEQUENCE LISTING

The instant application contains a Sequence Listing which has been submitted electronically in ASCII format and is hereby incorporated by reference in its entirety. Said ASCII copy, created on Aug. 13, 2014, is named MERCK-4072-D01_SL.txt and is 1686 bytes in size.

The invention relates to compounds selected from the group

| No. | Structure/name |
|---|---|
| "A1" | 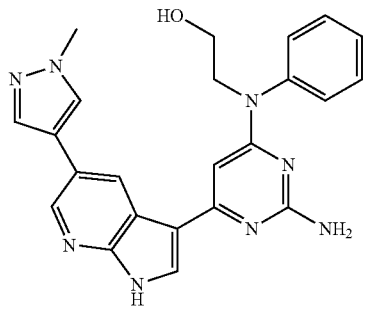<br>N4-(3-Fluorophenyl)-N4-methyl-6-[5-(1-methyl-1H-pyrazol-4-yl)-1H-pyrrolo[2,3-b]pyridin-3-yl]pyrimidine-2,4-diamine |
| "A2" | 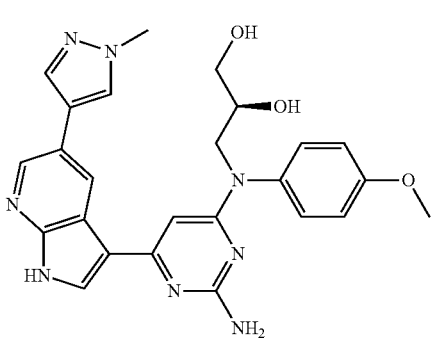<br>4-(1-Methyl-1-phenylethyl)-6-[5-(1-methyl-1H-pyrazol-4-yl)-1H-pyrrolo[2,3-b]pyridin-3-yl]pyrimidin-2-ylamine |
| "A3" | 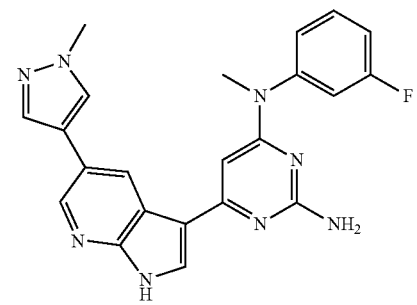 [SMILES: CN(c1cccc(F)c1)c1cc(-c2c[nH]c3ncc(-c4cnn(C)c4)cc23)nc(N)n1]<br>4-[5-(1-Methyl-1H-pyrazol-4-yl)-1H-pyrrolo[2,3-b]pyridin-3-yl]-6-(1-phenylcyclopropyl)pyrimidin-2-ylamine |
| "A4" | 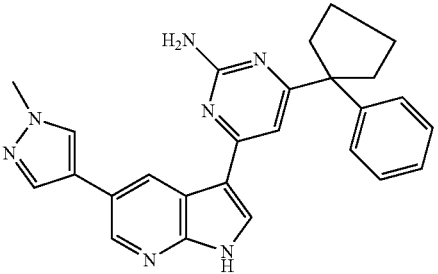<br>2-({2-Amino-6-[5-(1-methyl-1H-pyrazol-4-yl)-1H-pyrrolo[2,3-b]-pyridin-3-yl]pyrimidin-4-yl}phenylamino)ethanol |
| "A5" | 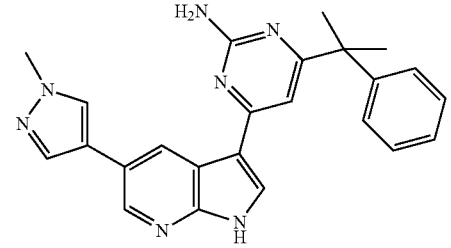 [SMILES: Cn1cc(-c2cnc3[nH]cc(-c4cc(C(C)(C)c5ccccc5)nc(N)n4)c3c2)cn1]<br>(S)-3-[{2-Amino-6-[5-(1-methyl-1H-pyrazol-4-yl)-1H-pyrrolo-[2,3-b]pyridin-3-yl]pyrimidin-4-yl}-(4-methoxyphenyl)amino]-propane-1,2-diol |
| "A6" | 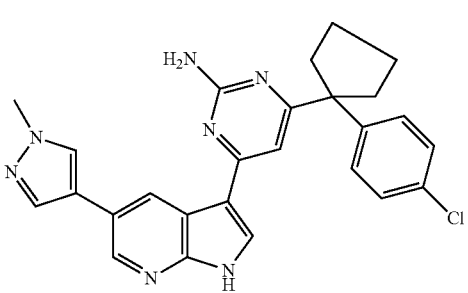 [SMILES: Cn1cc(-c2cnc3[nH]cc(-c4cc(C5(c6ccc(Cl)cc6)CCCC5)nc(N)n4)c3c2)cn1]<br>4-[5-(1-Methyl-1H-pyrazol-4-yl)-1H-pyrrolo[2,3-b]pyridin-3-yl]-6-(1-phenylcyclopentyl)pyrimidin-2-ylamine |
| "A7" | 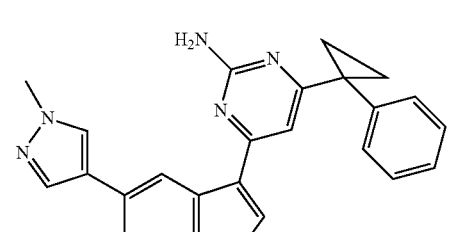<br>4-[1-(4-Chlorophenyl)cyclopentyl]-6-[5-(1-methyl-1H-pyrazol-4-yl)-1H-pyrrolo[2,3-b]pyridin-3-yl]pyrimidin-2-ylamine |

| No. | Structure/name |
|---|---|
| "A8" | 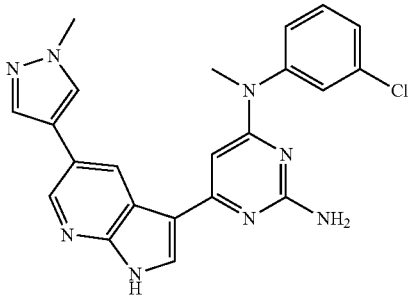 [SMILES: CN(c1cccc(Cl)c1)c1cc(-c2c[nH]c3ncc(-c4cnn(C)c4)cc23)nc(N)n1]<br>N4-(3-Chlorophenyl)-N4-methyl-6-[5-(1-methyl-1H-pyrazol-4-yl)-1H-pyrrolo[2,3-b]pyridin-3-yl]pyrimidine-2,4-diamine |
| "A9" | 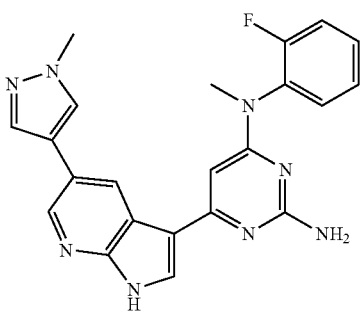 [SMILES: CN(c1cc(-c2c[nH]c3ncc(-c4cnn(C)c4)cc23)nc(N)n1)c1ccccc1F]<br>N4-(2-Fluorophenyl)-N4-methyl-6-[5-(1-methyl-1H-pyrazol-4-yl)-1H-pyrrolo[2,3-b]pyridin-3-yl]pyrimidine-2,4-diamine |
| "A10" | 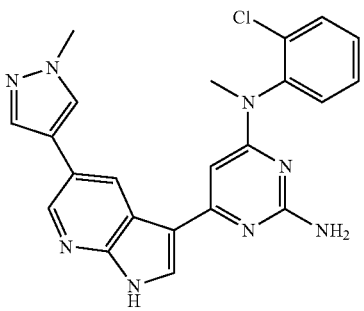 [SMILES: CN(c1cc(-c2c[nH]c3ncc(-c4cnn(C)c4)cc23)nc(N)n1)c1ccccc1Cl]<br>N4-(2-Chlorophenyl)-N4-methyl-6-[5-(1-methyl-1H-pyrazol-4-yl)-1H-pyrrolo[2,3-b]pyridin-3-yl]pyrimidine-2,4-diamine |
| "A11" | 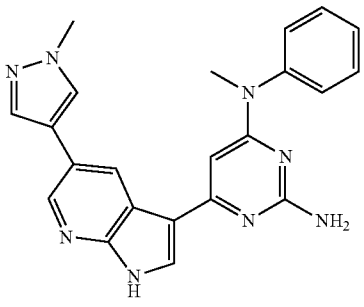 [SMILES: CN(c1ccccc1)c1cc(-c2c[nH]c3ncc(-c4cnn(C)c4)cc23)nc(N)n1]<br>N4-Methyl-6-[5-(1-methyl-1H-pyrazol-4-yl)-1H-pyrrolo[2,3-b]pyridin-3-yl]-N4-phenylpyrimidine-2,4-diamine |
| "A12" | 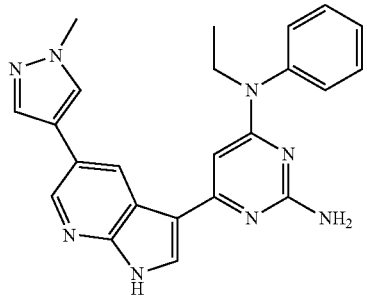 [SMILES: CCN(c1ccccc1)c1cc(-c2c[nH]c3ncc(-c4cnn(C)c4)cc23)nc(N)n1]<br>N4-Ethyl-6-[5-(1-methyl-1H-pyrazol-4-yl)-1H-pyrrolo[2,3-b]pyridin-3-yl]-N4-phenylpyrimidine-2,4-diamine |
| "A13" | 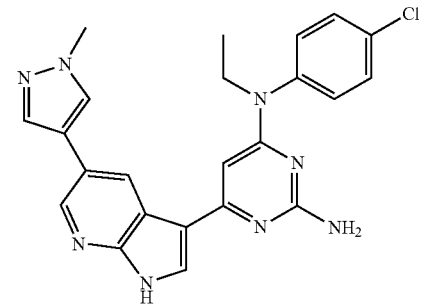 [SMILES: CCN(c1ccc(Cl)cc1)c1cc(-c2c[nH]c3ncc(-c4cnn(C)c4)cc23)nc(N)n1]<br>N4-(4-Chlorophenyl)-N4-ethyl-6-[5-(1-methyl-1H-pyrazol-4-yl)-1H-pyrrolo[2,3-b]pyridin-3-yl]pyrimidine-2,4-diamine |
| "A14" | 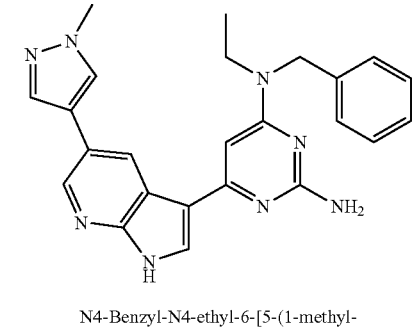<br>N4-Benzyl-N4-ethyl-6-[5-(1-methyl-1H-pyrazol-4-yl)-1H-pyrrolo[2,3-b]pyridin-3-yl]pyrimidine-2,4-diamine |
| "A15" | 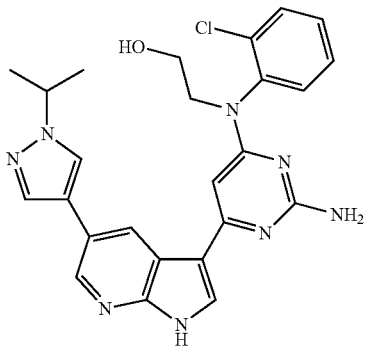 [SMILES: CC(C)n1cc(-c2cnc3[nH]cc(-c4cc(N(CCO)c5ccccc5Cl)nc(N)n4)c3c2)cn1]<br>2-[{2-Amino-6-[5-(1-isopropyl-1H-pyrazol-4-yl)-1H-pyrrolo[2,3-b]pyridin-3-yl]pyrimidin-4-yl}-(2-chlorophenyl)amino]-ethanol |

| No. | Structure/name |
|---|---|
| "A16" | 2-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]ethanol |
| "A17" | 4-(5-Fluoro-2,3-dihydroindol-1-yl)-6-[5-(1-methyl-1H-pyrazol-4-yl)-1H-pyrrolo[2,3-b]pyridin-3-yl]pyrimidin-2-ylamine |
| "A18" | 4-(5-Fluoro-2,3-dihydroindol-1-yl)-6-[5-(1-isopropyl-1H-pyrazol-4-yl)-1H-pyrrolo[2,3-b]pyridin-3-yl]pyrimidin-2-ylamine |
| "A19" | N4-(2-Chlorophenyl)-6-[5-(1-isopropyl-1H-pyrazol-4-yl)-1H-pyrrolo[2,3-b]pyridin-3-yl]-N4-methylpyrimidine-2,4-diamine |
| "A20" | N4-Ethyl-6-[5-(1-methyl-1H-pyrazol-4-yl)-1H-pyrrolo[2,3-b]-pyridin-3-yl]-N4-1,3,4-thiadiazol-2-ylpyrimidine-2,4-diamine |
| "A21" | 1-({2-Amino-6-[5-(1-methyl-1H-pyrazol-4-yl)-1H-pyrrolo[2,3-b]-pyridin-3-yl]pyrimidin-4-yl}phenylamino)-3-methoxypropan-2-ol |
| "A22" | 3-[{2-Amino-6-[5-(1-methyl-1H-pyrazol-4-yl)-1H-pyrrolo[2,3-b]-pyridin-3-yl]pyrimidin-4-yl}-(2,3-dihydroxypropyl)amino]-benzonitrile |

TABLE-continued

| No. | Structure/name |
|---|---|
| "A23" | 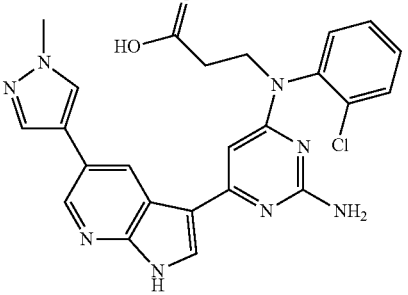<br>3-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]propionic acid |
| "A24" | 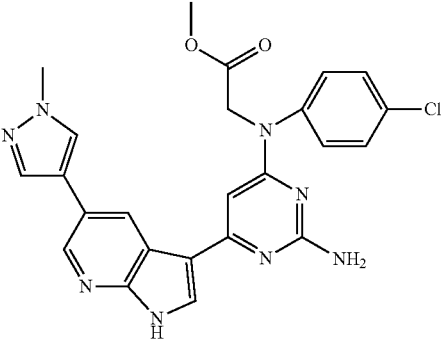 [SMILES: COC(=O)CN(c1ccc(Cl)cc1)c1cc(-c2c[nH]c3ncc(-c4cnn(C)c4)cc23)nc(N)n1]<br>Methyl [{2-amino-6-[5-(1-methyl-1H-pyrazol-4-yl)-1H-pyrrolo-[2,3-b]pyridin-3-yl]pyrimidin-4-yl}-(4-chlorophenyl)amino]acetate |
| "A25" | 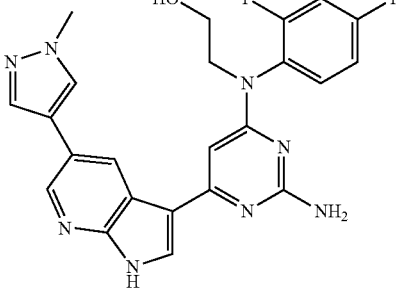<br>2-[{2-Amino-6-[5-(1-methyl-1H-pyrazol-4-yl)-1H-pyrrolo[2,3-b]-pyridin-3-yl]pyrimidin-4-yl}-(2,4-difluorophenyl)amino]ethanol |
| "A26" | 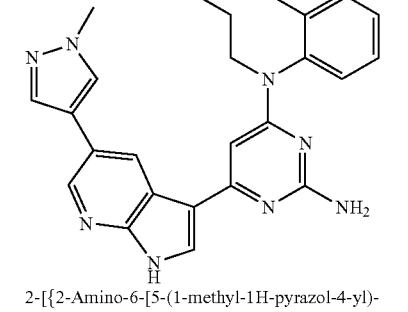<br>2-[{2-Amino-6-[5-(1-methyl-1H-pyrazol-4-yl)-1H-pyrrolo[2,3-b]-pyridin-3-yl]pyrimidin-4-yl}-(2-fluorophenyl)amino]ethanol |
| "A27" | 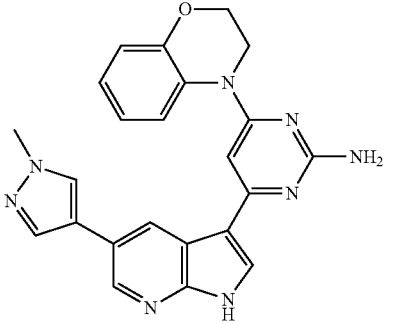 [SMILES: Cn1cc(-c2cnc3[nH]cc(-c4cc(N5CCOc6ccccc65)nc(N)n4)c3c2)cn1]<br>4-(2,3-Dihydrobenzo-1,4-oxazin-4-yl)-6-[5-(1-methyl-1H-pyrazol-4-yl)-1H-pyrrolo[2,3-b]pyridin-3-yl]pyrimidin-2-ylamine |
| "A28" | 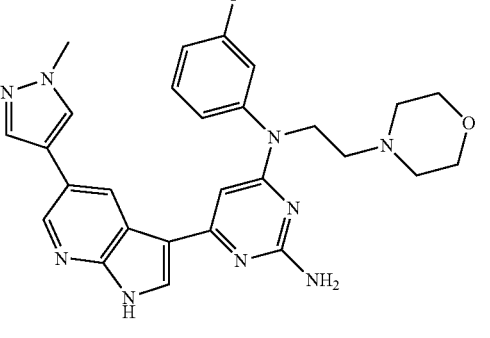<br>N4-(3-Fluorophenyl)-6-[5-(1-methyl-1H-pyrazol-4-yl)-1H-pyrrolo[2,3-b]pyridin-3-yl]-N4-(2-morpholin-4-ylethyl)pyrimidine-2,4-diamine |
| "A29" | 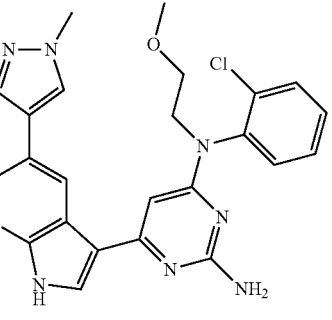<br>N4-(2-Chlorophenyl)-N4-(2-methoxyethyl)-6-[5-(1-methyl-1H-pyrazol-4-yl)-1H-pyrrolo[2,3-b]pyridin-3-yl]pyrimidine-2,4-diamine |

| No. | Structure/name |
|---|---|
| "A30" | 3-({2-Amino-6-[5-(1-methyl-1H-pyrazol-4-yl)-1H-pyrrolo[2,3-b]-pyridin-3-yl]pyrimidin-4-yl}phenylamino)propionitrile |
| "A30a" | (3-Fluorophenyl)methyl-{6-[5-(1-methyl-1H-pyrazol-4-yl)-1H-pyrrolo[2,3-b]pyridin-3-yl]pyrimidin-4-yl}amine |
| "A31" | N4-(3-Aminopropyl)-6-[5-(1-methyl-1H-pyrazol-4-yl)-1H-pyrrolo[2,3-b]pyridin-3-yl]-N4-phenylpyrimidine-2,4-diamine |
| "A32" | N4-(3-Aminopropyl)-6-[5-(1-methyl-1H-pyrazol-4-yl)-1H-pyrrolo-[2,3-b]pyridin-3-yl]-N4-(2-methylpyridin-4-yl)pyrimidine-2,4-diamine |
| "A33" | 3-[{2-Amino-6-[5-(1-methyl-1H-pyrazol-4-yl)-1H-pyrrolo[2,3-b]-pyridin-3-yl]pyrimidin-4-yl}-(2-methylpyridin-4-yl)amino]-propionitrile |
| "A34" | 4-[5-(1-Methyl-1H-pyrazol-4-yl)-1H-pyrrolo[2,3-b]pyridin-3-yl]-6-[1-(2-methylpyridin-4-yl)cyclopropyl]pyrimidin-2-ylamine |

| No. | Structure/name |
|---|---|
| "A35" | 3-({2-Amino-6-[5-(1-methyl-1H-pyrazol-4-yl)-1H-pyrrolo[2,3-b]-pyridin-3-yl]pyrimidin-4-yl}phenylamino)propionamide |
| "A36" | 3-[{2-Amino-6-[5-(1-methyl-1H-pyrazol-4-yl)-1H-pyrrolo[2,3-b]-pyridin-3-yl]pyrimidin-4-yl}-(2-methylpyridin-4-yl)amino]-propionamide |
| "A37" | N4-(2-Methoxyethyl)-6-[5-(1-methyl-1H-pyrazol-4-yl)-1H-pyrrolo[2,3-b]pyridin-3-yl]-N4-(2-methylpyridin-4-yl)pyrimidine-2,4-diamine |
| "A38" | N4-(2-Methoxyethyl)-6-[5-(1-methyl-1H-pyrazol-4-yl)-1H-pyrrolo[2,3-b]pyridin-3-yl]-N4-(1-methylpyrazol-4-yl)pyrimidine-2,4-diamine |
| "A39" | N4-(3-Aminopropyl)-6-[5-(1-methyl-1H-pyrazol-4-yl)-1H-pyrrolo[2,3-b]pyridin-3-yl]-N4-(2-chlorophenyl)pyrimidine-2,4-diamine |
| "A40" | 3-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]propionamide |

| No. | Structure/name |
|---|---|
| "A41" | 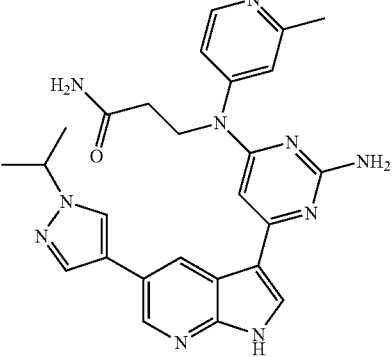<br>3-[{2-Amino-6-[5-(1-isopropyl-1H-pyrazol-4-yl)-1H-pyrrolo-[2,3-b]pyridin-3-yl]pyrimidin-4-yl}-(2-methylpyridin-4-yl)amino]-propionamide |
| "A42" | 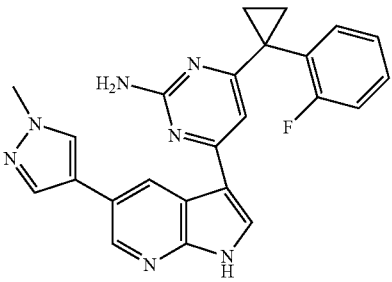 [SMILES: Cn1cc(-c2cnc3[nH]cc(-c4cc(C5(c6ccccc6F)CC5)nc(N)n4)c3c2)cn1]<br>4-[1-(2-Fluorophenyl)cyclopropyl]-6-[5-(1-methyl-1H-pyrazol-4-yl)-1H-pyrrolo[2,3-b]pyridin-3-yl]pyrimidin-2-ylamine |
| "A43" | 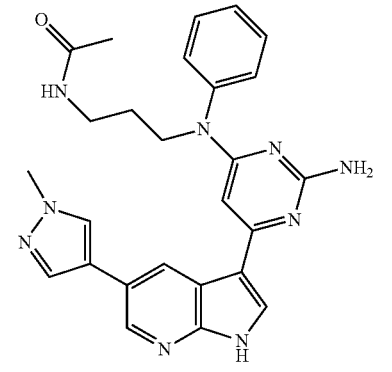 [SMILES: CC(=O)NCCCN(c1ccccc1)c1cc(-c2c[nH]c3ncc(-c4cnn(C)c4)cc23)nc(N)n1]<br>N-[3-({2-Amino-6-[5-(1-methyl-1H-pyrazol-4-yl)-1H-pyrrolo-[2,3-b]pyridin-3-yl]pyrimidin-4-yl}phenylamino)propyl]acetamide | and pharmaceutically usable salts, tautomers and stereoisomers thereof, including mixtures thereof in all ratios.

The invention was based on the object of finding novel compounds having valuable properties, in particular those which can be used for the preparation of medicaments.

Other heterocyclic compounds, such as pyrimidinyl-2-amine derivatives, are described in WO 2010/000364 or WO 2008/155000.

A crucial advantage of the compounds according to the invention is the fact that they are achiral compounds. Compared with the compounds described in WO 2010/000364, expensive and complex racemate resolution is superfluous in the case of the compounds according to the invention. In addition, the compounds according to the invention have advantages which are indicated in Table I in comparison with compounds from WO 2010/000364.

4-(Pyrrolopyridinyl)pyrimidinyl-2-amine derivatives are described by P. M. Fresneda et al. in Tetrahedron 57, 2355-2363 (2001).

4-(Pyrrolopyridinyl)pyrimidinyl-2-amine derivatives are described by A. Karpov in his dissertation, University of Heidelberg, April 2005.

Aminopyridine derivatives which carry a 2,2,6,6-tetramethylpiperidin-4-yl radical are described in WO 2004/089913 for the treatment of inflammatory and autoimmune diseases.

It has been found that the compounds according to the invention and salts and/or solvates thereof have very valuable pharmacological properties while being well tolerated.

In particular, they exhibit a cell proliferation/cell vitality-inhibiting action as antagonists or agonists. The compounds according to the invention can therefore be used for the combating and/or treatment of tumours, tumour growth and/or tumour metastases.

The antiproliferative action can be tested in a proliferation assay/vitality assay.

Accordingly, the compounds according to the invention or a pharmaceutically acceptable salt thereof are administered for the treatment of cancer, including solid carcinomas, such as, for example, carcinomas (for example of the lungs, pancreas, thyroid, bladder or colon), myeloid diseases (for example myeloid leukaemia) or adenomas (for example villous colon adenoma).

The tumours furthermore include monocytic leukaemia, brain, urogenital, lymphatic system, stomach, laryngeal and lung carcinoma, including lung adenocarcinoma and small-cell lung carcinoma, pancreatic and/or breast carcinoma.

The compounds are furthermore useful in the treatment of immune deficiency induced by HIV-1 (Human Immunodeficiency Virus Type 1).

Cancer-like hyperproliferative diseases are to be regarded as brain cancer, lung cancer, squamous epithelial cancer, bladder cancer, stomach cancer, pancreatic cancer, liver cancer, renal cancer, colorectal cancer, breast cancer, head cancer, neck cancer, oesophageal cancer, gynaecological cancer, thyroid cancer, lymphomas, chronic leukaemia and acute leukaemia. In particular, cancer-like cell growth is a disease which represents a target of the present invention. The present invention therefore relates to compounds according to the invention as medicaments and/or medicament active compounds in the treatment and/or prophylaxis of the said diseases and to the use of compounds according to the invention for the preparation of a pharmaceutical for the treatment and/or prophylaxis of the said diseases and to a process for the treatment of the said diseases comprising the administration of one or more compounds according to the invention to a patient in need of such an administration.

It can be shown that the compounds according to the invention have an antiproliferative action. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both the prevention of diseases and the treatment of pre-existing conditions. The prevention of proliferation/vitality is achieved by administration of the compounds according to the invention prior to the development of overt disease, for example for preventing tumour growth. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of a human disease.

The susceptibility of a particular cell to treatment with the compounds according to the invention can be determined by in vitro testing. Typically, a culture of the cell is incubated with a compound according to the invention at various concentrations for a period of time which is sufficient to allow the active agents to induce cell death or to inhibit cell proliferation, cell vitality or migration, usually between about one hour and one week. In vitro testing can be carried out using cultivated cells from a biopsy sample. The amount of cells remaining after the treatment are then determined.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

There are many diseases associated with deregulation of cell proliferation and cell death (apoptosis). The conditions of interest include, but are not limited to, the following. The compounds according to the invention are suitable for the treatment of various conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, coronary vascular disease after grafting, vein graft stenosis, perianastomatic prosthetic restenosis, restenosis after angioplasty or stent placement, and the like.

The compounds according to the invention, also act as regulators, modulators or inhibitors of protein kinases, in particular of the serine/threonine kinase type, which include, inter alia, phosphoinositide-dependent kinase 1 (PDK1). The compounds according to the invention exhibit a certain action in the inhibition of the serine/threonine kinase PDK1.

PDK1 phosphorylates and activates a sub-group of the AGC protein kinase family, comprising PKB, SGK, S6K and PKC isoforms. These kinases are involved in the PI3K signal transduction pathway and control basic cellular functions, such as survival, growth and differentiation. PDK1 is thus an important regulator of diverse metabolic, proliferative and life-sustaining effects.

Diseases caused by protein kinases are characterised by anomalous activity or hyperactivity of such protein kinases. Anomalous activity relates to either: (1) expression in cells which do not usually express these protein kinases; (2) increased kinase expression, which results in undesired cell proliferation, such as cancer; (3) increased kinase activity, which results in undesired cell proliferation, such as cancer, and/or in hyperactivity of the corresponding protein kinases. Hyperactivity relates either to amplification of the gene which encodes for a certain protein kinase, or the generation of an activity level which can be correlated with a cell proliferation disease (i.e. the severity of one or more symptoms of the cell proliferation disease increases with increasing kinase level).

The bioavailability of a protein kinase may also be influenced by the presence or absence of a set of binding proteins of this kinase.

The most important types of cancer that can be treated using a compound according to the invention include colorectal cancer, small-cell lung cancer, non-small-cell lung cancer, multiple myeloma as well as renal cell carcinoma and endometrium carcinoma, particularly also types of cancer in which PTEN is mutated, inter alia breast cancer, prostate cancer and glioblastoma.

In addition, the compounds according to the invention can be used to achieve additive or synergistic effects in certain existing cancer chemotherapies and radiotherapies and/or to restore the efficacy of certain existing cancer chemotherapies and radiotherapies.

The invention also relates to the optically active forms (stereoisomers), salts, the enantiomers, the racemates, the diastereomers and the hydrates and solvates of these compounds. Solvate of the compounds are taken to mean adductions of inert solvent molecules onto the compounds which form owing to their mutual attractive force. Solvate are, for example, mono- or dihydrates or alcoholates.

The invention naturally also relates to the solvates of the salts of the compounds according to the invention."

Pharmaceutically usable derivatives are taken to mean, for example, the salts of the compounds according to the invention and also so-called prodrug compounds.

Prodrug derivatives are taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active compound which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side effects or also the reduction in the advance of a disease, condition or disorder.

The expression "therapeutically effective amount" also encompasses the amounts which are effective for increasing normal physiological function.

The invention also relates to the use of mixtures of the compounds according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The compounds according to the invention are preferably prepared from a 7-azaindole derivative and an iodopyrimidine derivative in a Suzuki reaction. Depending on the conditions used, the reaction time is between a few minutes and 14 days, the reaction temperature is between about −30° and 140°, normally between 0° and 100°, in particular between about 60° and about 90° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. Particular preference is given to methanol, dimethoxyethane or dioxane.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentane-propionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds according to the invention are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds according to the invention are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active compound which comprises a compound according to the invention in the form of one of its salts, in particular if this salt form imparts improved pharmacokinetic properties on the active compound compared with the free form of the active compound or any other salt form of the active compound used earlier. The pharmaceutically acceptable salt form of the active compound can also provide this active compound for the first time with a desired pharmacokinetic property which it did not have earlier and can even have a positive influence on the pharmacodynamics of this active compound with respect to its therapeutic efficacy in the body.

The invention furthermore relates to medicaments comprising at least one compound according to the invention and/or pharmaceutically usable salts, tautomers and stereoisomers thereof, including mixtures thereof in all ratios, and optionally excipients and/or adjuvants.

Pharmaceutical formulations can be administered in the form of dosage units which comprise a predetermined amount of active compound per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Preferred dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active compound with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, can likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a prespecified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and physiologically functional salts and solvates thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the physiologically functional salts and solvates thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active compound can be delivered from the plaster by iontophoresis, as described in general terms in Pharmaceutical Research, 3(6), 318 ff. (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active compound can be employed either with a paraffinic or a water-miscible cream base. Alternatively, the active compound can be formulated to give a cream with an oil-in-water cream base or a water-in-oil base.

Pharmaceutical formulations adapted for topical application to the eye include eye drops, in which the active compound is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound according to the invention depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable salts, solvates and stereoisomers thereof, including mixtures thereof in all ratios, and at least one further medicament active compound.

The invention also relates to a set (kit) consisting of separate packs of
(a) an effective amount of a compound according to the invention and/or pharmaceutically usable salts, solvates and stereoisomers thereof, including mixtures thereof in all ratios, and
(b) an effective amount of a further medicament active compound.

The set comprises suitable containers, such as boxes, individual bottles, bags or ampoules. The set may, for example, comprise separate ampoules, each containing an effective amount of a compound according to the invention and/or pharmaceutically usable salts, solvates and stereoisomers thereof, including mixtures thereof in all ratios, and an effective amount of a further medicament active compound in dissolved or lyophilised form.

Use

The present compounds are suitable as pharmaceutical active compounds for mammals, especially for humans, in the treatment and control of cancer diseases.

The present invention encompasses the compounds according to the invention and/or physiologically acceptable salts and solvates thereof for use for the treatment or prevention of cancer. Preferred carcinomas for the treatment originate from the group cerebral carcinoma, urogenital tract carcinoma, carcinoma of the lymphatic system, stomach carcinoma, laryngeal carcinoma and lung carcinoma bowel cancer. A further group of preferred forms of cancer are monocytic leukaemia, lung adenocarcinoma, small-cell lung carcinomas, pancreatic cancer, glioblastomas and breast carcinoma.

The invention also relates to a method for the treatment of a patient suffering from cancer, in which an effective amount of a compound of the formula I according to the invention and/or physiologically acceptable salts and solvates thereof is administered.

The present invention also encompasses the use of the compounds according to the invention and/or physiologically acceptable salts and solvates thereof for the preparation of a medicament for the treatment or prevention of cancer.

Also encompassed are the compounds according to the invention and/or physiologically acceptable salts and solvates thereof for use for the treatment and/or control of a tumour-induced disease in a mammal, in which to this method a therapeutically effective amount of a compound according to the invention is administered to a sick mammal in need of such treatment. The therapeutic amount varies according to the particular disease and can be determined by the person skilled in the art without undue effort.

Particular preference is given to the use for the treatment of a disease, where the disease is a solid tumour.

The solid tumour is preferably selected from the group of tumours of the squamous epithelium, the bladder, the stomach, the kidneys, of head and neck, the oesophagus, the cervix, the thyroid, the intestine, the liver, the brain, the prostate, the urogenital tract, the lymphatic system, the stomach, the larynx and/or the lung.

The solid tumour is furthermore preferably selected from the group lung adenocarcinoma, small-cell lung carcinomas, pancreatic cancer, glioblastomas, colon carcinoma and breast carcinoma.

Preference is furthermore given to the use for the treatment of a tumour of the blood and immune system, preferably for the treatment of a tumour selected from the group of acute myeloid leukaemia, chronic myeloid leukaemia, acute lymphatic leukaemia and/or chronic lymphatic leukaemia.

The invention furthermore relates to the use of the compounds according to the invention for the treatment of bone pathologies, where the bone pathology originates from the group osteosarcoma, osteoarthritis and rickets.

The compounds according to the invention may also be administered at the same time as other well-known therapeutic agents that are selected for their particular usefulness against the condition that is being treated.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and further angiogenesis inhibitors.

The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenylretinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors. Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cisaminedichloro(2-methylpyridine)platinum, benzylguanine, glufosfamide, GPX100, (trans,trans,trans)bis-mu-(hexane-1,6-diamine)-mu-[diamineplatinum(II)]bis[diamine(chloro)platinum(II)]tetrachloride, diarisidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide (SEQ ID NO: 11 TDX258 and BMS188797.

Topoisomerase inhibitors are, for example, topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)-dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N41-[2(diethylamino)ethylamino]-7-methoxy-9-oxo-9H-thioxanthen-4-ylmethyliformamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and anti-metabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,1'-diazatetracyclo(7.4.1.0.0)tetradeca-2,4,6-trien-9-ylacetic acid ester, swainsonine, lometrexol, dexrazoxane, methioninase, 2'-cyano-2'-deoxy-N4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Evidence of the Action of Pharmacological Inhibitors on the Proliferation/Vitality of Tumour Cells in vitro 1. Background In the present experiment description, the inhibition of tumour cell proliferation/tumour cell vitality by active compounds is described. The cells are sown in a suitable cell density in microtitre plates (96-well format) and the test substances are added in the form of a concentration series. After four further days of cultivation in serum-containing medium, the tumour cell proliferation/tumour cell vitality can be determined by means of an Alamar Blue test system.

2. Experimental Procedure 2.1 Cell Culture

For example commercially available colon carcinoma cell lines, ovary cell lines, prostate cell lines or breast cell lines, etc. The cells are cultivated in medium. At intervals of several days, the cells are detached from the culture dishes with the aid of trypsin solution and sown in suitable dilution in fresh medium. The cells are cultivated at 37° Celsius and 10% $CO_2$.

2.2. Sowing of the Cells

A defined number of cells (for example 2000 cells) per culture/well in a volume of 180 µl of culture medium are sown in microtitre plates (96 well cell-culture plates) using a multichannel pipette. The cells are subsequently cultivated in a $CO_2$ incubator (37° C. and 10% $CO_2$).

2.3. Addition of the Test Substances

The test substances are dissolved, for example, in DMSO and subsequently employed in corresponding concentration (if desired in a dilution series) in the cell culture medium. The dilution steps can be adapted depending on the efficiency of the active compounds and the desired spread of the concentrations. Cell culture medium is added to the test substances in corresponding concentrations. The addition of the test substances to the cells can take place on the same day as the sowing of the cells. To this end, in each case 20 µl of substance solution from the predilution plate are added to the cultures/wells. The cells are cultivated for a further 4 days at 37° Celsius and 10% $CO_2$.

2.4. Measurement of the Colour Reaction

In each case, 20 µl of Alamar Blue reagent are added per well, and the microtitre plates are incubated, for example, for a further seven hours in a CO2 incubator (at 37° C. and 10% CO2). The plates are measured in a reader with a fluorescence filter at a wavelength of 540 nm. The plates can be shaken gently immediately before the measurement.

3. Evaluation

The absorbance value of the medium control (no cells and test substances used) is subtracted from all other absorbance values. The controls (cells without test substance) are set equal to 100 percent, and all other absorbance values are set in relation thereto (for example in % of control):

Calculation:

$$\frac{100*(\text{value with cells and test substance} - \text{value of medium control})}{(\text{value with cells} - \text{value of medium control})}$$

$IC_{50}$ values (50% inhibition) are determined with the aid of statistics programs, such as, for example, RS1.

$IC_{50}$ data of compounds according to the invention are indicated in Table 1.

4. Test for the Inhibition of PDK1

The experimental batches are carried out in a flashplate system with 384 wells/microtitration plate.

In each case, the PDK1 sample $His_6$-PDK1(Δ1-50)(3.4 nM) ("$His_6$" disclosed as SEQ ID NO: 2), the PDK1 substrate biotin-bA-bAKTFCGTPEYLAPEVRREPRILSEE-EQEMFRDFDYIADWC (SEQ ID NO: 3) (400 nM), 4 µM ATP (with 0.2 µCi of $^{33}$P-ATP/well) and the test substance in 50 µl of conventional experimental solution per well are incubated at 30° C. for 60 min. The test substances are employed in corresponding concentrations (if desired in a dilution series). The control is carried out without test substance. The reaction is stopped using standard methods and washed. The activity of the kinase is measured via the incorporated radioactivity in top count. In order to determine the non-specific kinase reaction (blank value), the experimental batches are carried out in the presence of 100 nM staurosporine.

5. Evaluation

The radioactivity (decompositions per minute) of the blank value (no use of test substance in the presence of staurosporine) is subtracted from all other radioactivity values. The controls (kinase activity without test substance) are set equal to 100 percent and all other radioactivity values (after subtracting the blank value) are expressed set in relation thereto (for example in % of the control).

Calculation:

$$\frac{100 * (\text{value of the kinase activity with test substance} - \text{blank value})}{(\text{value of the control} - \text{blank value})} = \% \text{ of the control}$$

$IC_{50}$ values (50% inhibition) are determined with the aid of statistics programmes, such as, for example, RS1. $IC_{50}$ data of compounds according to the invention are indicated in Table 1.

| Material | Order No. | Manufacturer |
|---|---|---|
| Microtitre plates for cell culture (Nunclon Surface 96-well plate) | | 167008 Nunc |
| DMEM | P04-03550 | Pan Biotech |
| PBS (10x) Dulbecco | 14200-067 | Gibco |
| 96-well plates (polypropylene) | | 267334 Nunc |
| AlamarBlue ™ | BUF012B | Serotec |
| FCS | 1302 | Pan Biotech GmbH |
| Trypsin/EDTA solution 10x | L 2153 | Biochrom AG |
| 75 cm² culture bottles | 353136 | BD Falcon |
| A2780 | 93112519 | ECACC |
| Colo205 | CCL222 | ATCC |
| MCF7 | HTB22 | ATCC |
| PC3 | CRL-1435 | ATCC |
| 384-well flash plates | SMP410A001PK | Perkin Elmer |

APCI-MS (atmospheric pressure chemical ionisation - mass spectrometry) (M + H)⁺.

Method for the Cellular Testing of PDK1 Kinase Inhibitors in PC3 Cells

The cellular assay for the determination of the PDK1 kinase activity is carried out as a Luminex assay in the 96-well format. PC3 cells are sown at 20,000 cells per well in 100 μl of medium (45% of RPMI1460/45% of Ham's F12/10% of FCS) and incubated on the following day for 30 min with a serial dilution of the test substance (7 concentrations) under serum-free conditions. The cells are subsequently lysed using 90 μl of lysis buffer (20 mM tris/HCl pH 8.0, 150 mM NaCl, 1% of NP40, 10% of glycerol, 1% of phosphatase inhibitor I, 1% of phosphatase inhibitor II, 0.1% of protease inhibitor cocktail III, 0.01% of benzonase) per well, and the lysates are separated off from insoluble cell constituents by means of centrifugation through a 96-well filter plate (0.65 μm). The lysates are incubated overnight at 4° C. with shaking with Luminex beads to which an anti-total PKB antibody is coupled. The detection is carried out on the following day by addition of a phospho-T308-PKB antibody and a species-specific peroxidase-labelled secondary antibody. The detection of phospho-T308-PKB is carried out by measurement in a Luminex100 instrument by determination of 100 events per cavity in a measurement time of 60 sec. As pharmacological blank, the signals obtained from cells which have been treated with 10 μM staurosporine are subtracted from all other batches. The control value used for maximum phosphorylation of PKB on T308 are the signals from cells which have only been treated with the solvent (0.3% of DMSO). The values of the batches treated with test substance are calculated therefrom as percentage of control, and $IC_{50}$ values are determined by means of RS1.

Description of the Preparative HPLC Method:

Column type: Chromolith-prep RP-18e 100-25, detection: UV 230 nM

Solvent A: water+0.1% of trifluoroacetic acid

Solvent B: acetonitrile+0.1% of trifluoroacetic acid

Flow rate: 30 ml/min

Gradient: 0 min 99% of water, 10 min 1% of water

Description of the Preparative HPLC Method:

Column type: Chromolith-prep RP-18e 100-25, detection: UV 230 nM

Solvent A: water+0.1% of trifluoroacetic acid

Solvent B: acetonitrile+0.1% of trifluoroacetic acid

Flow rate: 30 ml/min

Gradient: 0 min 99% of water, 10 min 1% of water

Description of the HPLC/MS Method:

Equipment:

Agilent 1200 series

Column:

Chromolith® SpeedRod RP18e 50-4.6

Eluents:

A=H₂O+0.05% of HCOOH

B=CH₃CN+0.04% of HCOOH

Method: polar

Flow rate: 2.4 ml/min

Max press.: 150

Gradient:

0 min: 4% of B, 2.8 min: 100% of B; 3.3 min 100% of B; 3.4 min 4% of B

Detection wave length:

220 nm

Y: % of B

X: time

EXAMPLES

Synthesis of 1-benzenesulfonyl-3-iodo-5-(1-methyl-1H-pyrazol-4-yl)-1H-pyrrolo[2,3-b]pyridine

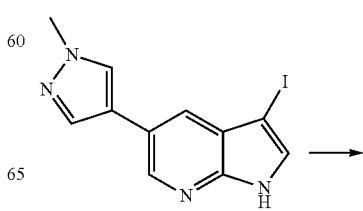

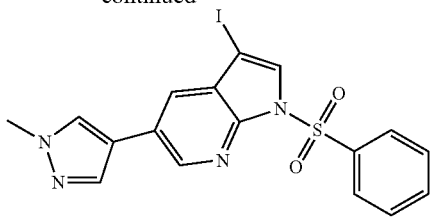

The 3-iodo-5-(1-methylpyrazol-4-yl)-7-azaindole prepared in accordance with WO 2008155000 (34 g) is suspended in 350 ml of dichloromethane, and 43.5 ml of triethylamine and 2.6 g of 4-(dimethylamino)pyridine are added. 17.5 ml of benzenesulfonyl chloride which has previously been diluted with 150 of dichloromethane are added to this mixture. After 2 h, the reaction is complete. The organic phase is extracted three times with water, and the organic phase is dried over sodium sulfate. After removal of the solvent, the residue is taken up in ethyl acetate, the precipitate is filtered off, rinsed with ethyl acetate, and the product is dried in air to give 44 g (90%) of beige crystals; (Rt: 2.467 min; M+H$^+$: 464.9).

The following derivatives are also produced by this route:

1-benzenesulfonyl-3-iodo-5-(1-isopropyl-1H-pyrazol-4-yl)-1H-pyrrolo[2,3-b]-pyridine (89%; Rt: 2.620 min; M+H$^+$: 493.0);

1-benzenesulfonyl-5-(1-tert-butyl-1H-pyrazol-4-yl)-3-iodo-1H-pyrrolo [2,3-b]-pyridine (88%; Rt: 2.730 min; M+H$^+$: 507.0);

1-benzenesulfonyl-5-(1-difluoromethyl-1H-pyrazol-4-yl)-3-iodo-1H-pyrrolo-[2,3-b]pyridine (90%; Rt: 2.560 min; M+H$^+$: 501.0);

1-[4-(1-benzenesulfonyl-3-iodo-1H-pyrrolo[2,3-b]pyridin-5-yl)pyrazol-1-yl]-3-methoxypropan-2-ol (60%; Rt: 2.289 min; M+H$^+$: 539.0);

1-benzenesulfonyl-3-iodo-5-{1-[2-(tetrahydropyran-2-yloxy)ethyl]-1H-pyrazol-4-yl}-1H-pyrrolo[2,3-b]pyridine (45%; Rt: 2.614 min; M+H$^+$: 579.0);

1-benzenesulfonyl-5-bromo-3-iodo-1H-pyrrolo[2,3-b]pyridine (93%; Rt: 2.757 min; M+H$^+$: 462.80+464.80).

Synthesis of 1-benzenesulfonyl-5-(1-methyl-1H-pyrazol-4-yl)-3-(4,4,5,5-tetramethyl-1,3,2-dioxaborolan-2-yl)-1H-pyrrolo[2,3-b]pyridine

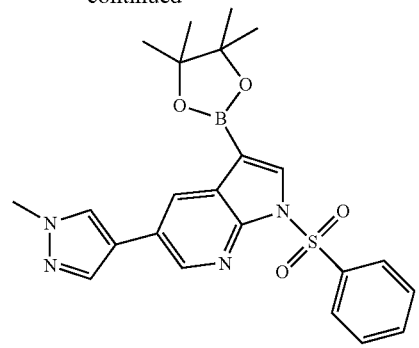

8 g of bis(pinacolato)diboron and 6.4 g of potassium acetate are added to a solution of 10 g of 1-benzenesulfonyl-3-iodo-5-(1-methyl-1H-pyrazol-4-yl)-1H-pyrrolo[2,3-b]pyridine in 160 ml of DMF. This mixture is degassed in vacuo, and finally 1.8 g of 1,1'bis(diphenylphosphino)ferrocenepalladium(II) dichloride in a complex with dichloromethane are added. The batch is stirred at 80° C. for 12. After removal of the solvent in vacuo, the residue is partitioned between water and ethyl acetate, unbdissolved components are filtered off through kieselguhr with suction, and the solution remaining is separated into the phases. The organic phase is evaporated, and the residue is chromatographed on silica gel, giving 4.5 g (45%) of beige crystals.

The following derivatives are also produced by this route:

1-benzenesulfonyl-5-(1-isopropyl-1H-pyrazol-4-yl)-3-(4,4,5,5-tetramethyl-1,3,2-dioxaborolan-2-yl)-1H-pyrrolo[2,3-b]pyridine (92%; Rt: 2.752 min; M+H$^+$: 493.20);

1-benzenesulfonyl-5-(1-tert-butyl-1H-pyrazol-4-yl)-3-(4,4,5,5-tetramethyl-1,3,2-dioxaborolan-2-yl)-1H-pyrrolo[2,3-b]pyridine (86%; Rt: 2.785 min; M+H$^+$: 507.20);

1-benzenesulfonyl-5-(1-difluoromethyl-1H-pyrazol-4-yl)-3-(4,4,5,5-tetramethyl-1,3,2-dioxaborolan-2-yl)-1H-pyrrolo[2,3-b]pyridine (26%; Rt: 2.701 min; M+H$^+$: 501.10);

1-{4-[1-benzenesulfonyl-3-(4,4,5,5-tetramethyl-1,3,2-dioxaborolan-2-yl)-1H-pyrrolo[2,3-b]pyridin-5-yl]pyrazol-1-yl}-3-methoxypropan-2-ol (5%; Rt: 2.615 min; M+H$^+$: 539.42);

1-benzenesulfonyl-5-{1-[2-(tetrahydropyran-2-yloxy)ethyl]-1H-pyrazol-4-yl}-3-(4,4,5,5-dioxaborolan-2-yl)-1H-pyrrolo[2,3-b]pyridine (17%; Rt: 2.731 min; M+H von N4-(3-fluorophenyl)-6-iodo-N4-methylpyrimidine-2,4-diamine

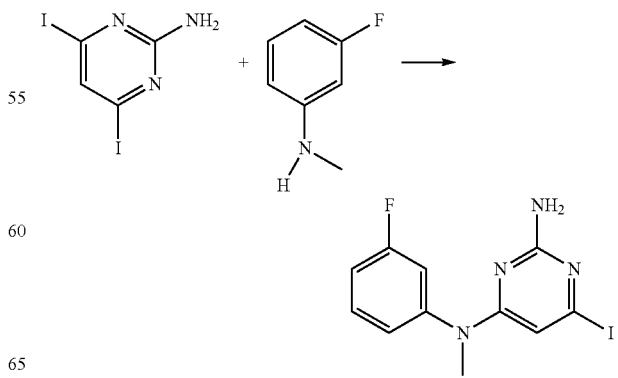

1 g of 4,6-diiodopyrimidin-2-ylamine and 380 mg of (3-fluorophenyl)methylamine are dissolved in 15 ml of ethanol, and 0.7 ml of 1N HCl is added. This mixture is irradiated in the microwave at 140° C. for 30 minutes. The solvent is subsequently removed in vacuo, the residue is partitioned between ethyl acetate and water, and a pH of 12 is set using 1N NaOH solution. After extraction of the organic phase, the combined organic phases are dried over sodium sulfate, evaporated and purified by chromatography on silica gel, giving 800 mg (81%) of brown crystals; (Rt: 2.010 min.; M+H+: 345.00).

Use of 4,6-dichloropyrimidin-2-ylamine enables N4-(3-fluorophenyl)-6-chloro-N4-methylpyrimidine-2,4-diamine to be prepared correspondingly (52%; Rt: 2.159 min.; M+H+: 253.00).

The following compounds are produced correspondingly:
3-[(2-amino-6-iodopyrimidin-4-yl)-(4-methoxyphenyl)amino]propane-1,2-diol (27%; Rt: 1.626 min.; M+H+: 417.00);
2-[(2-amino-6-iodopyrimidin-4-yl)phenylamino]ethanol (41%; Rt: 1.652 min.; M+H+: 357.00);
N4-(2-chlorophenyl)-6-iodo-N4-methylpyrimidine-2,4-diamine (56%; Rt: 2.133 min.; M+H+: 360.90);
N4-(2-bromophenyl)-6-iodo-N4-methylpyrimidine-2,4-diamine (27%; Rt: 2.126 min.; M+H+: 404.90+406.90);
N4-(3-chlorophenyl)-6-iodo-N4-methylpyrimidine-2,4-diamine (41%; Rt: 2.261 min.; M+H+: 360.90);
N4-(2-fluorophenyl)-6-iodo-N4-methylpyrimidine-2,4-diamine (32%; Rt: 2.046 min.; M+H+: 344.95);
N4-ethyl-6-iodo-N4-phenylpyrimidine-2,4-diamine (43%; Rt: 2.048 min.; M+H+: 341.00);
N4-(4-chlorophenyl)-N4-ethyl-6-iodopyrimidine-2,4-diamine (43%; Rt: 2.405 min.; M+H+: 375.95);
2-[(2-amino-6-iodopyrimidin-4-yl)-(2-chlorophenyl)amino]ethanol (49%; Rt: 1.191 min.; M+H+: 391.00)
2-[(2-amino-6-iodopyrimidin-4-yl)-(2,3-difluorophenyl)amino]ethanol (5%; Rt: 1.901 min.; M+H+: 393.00);
4-(5-fluoro-2,3-dihydroindol-1-yl)-6-iodopyrimidin-2-ylamin (62%; Rt: 2.204 min.; M+H+: 357.00);
3-[(2-amino-6-iodopyrimidin-4-yl)-(2,3-dihydroxypropyl)amino]benzonitrile (46%; Rt: 1.646 min.; M+H+: 412.00)
3-[(2-amino-6-iodopyrimidin-4-yl)-(2-chlorophenyl)amino]propionic acid (75%; Rt: 1.927 min.; M+H+: 418.90);
N4-(3-fluorophenyl)-6-iodo-N4-(2-morpholin-4-ylethyl)pyrimidine-2,4-diamine (55%; Rt: 1.601 min.; M+H+: 444.05);
2-[(2-amino-6-iodopyrimidin-4-yl)-(2,4-difluorophenyl)amino]ethanol (20%; Rt: 1.904 min.; M+H+: 393.00);
2-[(2-amino-6-iodopyrimidin-4-yl)-(2-fluorophenyl)amino]ethanol (16%; Rt: 1.808 min.; M+H+: 375.00);
4-(2,3-dihydrobenzo-1,4-oxazin-4-yl)-6-iodopyrimidin-2-ylamine (69%; Rt: 2.228 min.; M+H+: 355.00);
ethyl [(2-amino-6-iodopyrimidin-4-yl)-(4-chlorophenyl)amino]acetate (64%; Rt: 2.429 min.; M+H+: 433.00);
4-[(2-amino-6-iodopyrimidin-4-yl)-(2-hydroxyethyl)amino]-3-chlorobenzonitrile (24%; Rt: 1.895 min.; M+H+: 415.90);
N4-(2-chlorophenyl)-6-iodo-N4-(2-methoxyethyl)pyrimidine-2,4-diamine (12%; Rt: 2.191 min.; M+H+: 405.00);
3-[(2-amino-6-iodopyrimidin-4-yl)-(2-chlorophenyl)amino]propionitrile (37%; Rt: 2.173 min.; M+H+: 399.90);
6-chloro-N4-(3-fluorophenyl)-N4-methylpyrimidine-2,4-diamine (65%; Rt: 2.162 min.; M+H+: 253.00);
1-[(2-amino-6-chloropyrimidin-4-yl)phenylamino]-3-methoxypropan-2-ol (19%; Rt: 1.971 min.; M+H+: 309.10);
6-chloro-N4-pyrimidin-5-ylpyrimidine-2,4-diamine (16%; Rt: 1.687 min.; M+H+: 223.00);
6-chloro-N4-methyl-N4-(5-trifluoromethyl-1,3,4-thiadiazol-2-yl)pyrimidine-2,4-diamine (49%; Rt: 2.210 min.; M+H+: 311.00);
6-chloro-N4-ethyl-N-4-1,3,4-thiadiazol-2-ylpyrimidine-2,4-diamine (36%; Rt: 1.778 min.; M+H+: 357.00);
N4-benzyl-N4-ethyl-6-iodopyrimidine-2,4-diamine (52%; Rt: 1.942 min.; M+H+: 355.00).

Synthesis of 4-chloro-6-[1-(4-chlorophenyl)cyclopentyl]pyrimidin-2-ylamine

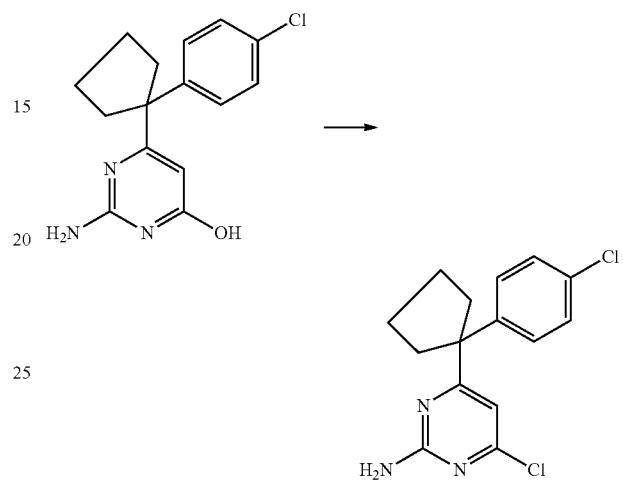

360 mg of 2-amino-6-[1-(4-chlorophenyl)cyclopentyl]pyrimidin-4-ol are dissolved in 10 ml of acetonitrile, and 0.8 ml of N-ethyldiisopropylamine is added under nitrogen. 0.5 ml of phosphoryl chloride are subsequently added slowly. The batch is boiled under reflux for 8 h in order to complete the reaction. All volatile constituents are subsequently removed in vacuo, and the batch is added to ice-water and dichloromethane. The organic phase is dried over sodium sulfate, filtered and evaporated. The residue obtained is employed in the subsequent reaction without further purification. (Rt: 2.694 min.; M+H+: 308.2+310.2).

The following compounds are prepared correspondingly:
4-chloro-6-(1-phenylcyclopentyl)pyrimidin-2-ylamine (Rt: 2.674 min.; M+H+: 274.10);
4-chloro-6-(1-phenylcyclopropyl)pyrimidin-2-ylamine (Rt: 2.468 min.; M+H+: 248.10);
4-chloro-6-(1-methyl-1-phenylethyl)pyrimidin-2-ylamine (Rt: 2.843 min.; M+H+: 248.10).

Synthesis of 3-[{2-amino-6-[5-(1-methyl-1H-pyrazol-4-yl)-1H-pyrrolo[2,3-b]-pyridin-3-yl]pyrimidin-4-yl}-(2-chlorophenyl)amino]propionitrile ("A30")

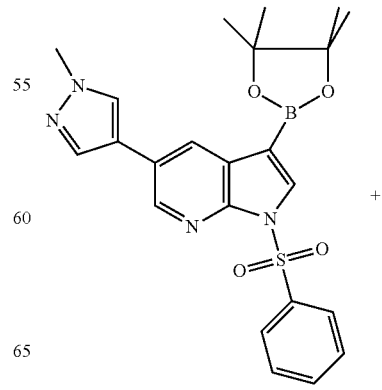

-continued

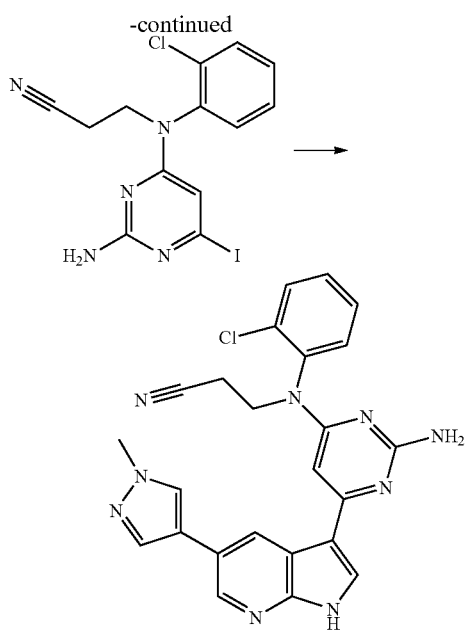

380 mg of 1-benzenesulfonyl-5-(1-methyl-1H-pyrazol-4-yl)-3-(4,4,5,5-tetramethyl-1,3,2-dioxaborolan-2-yl)-1H-pyrrolo[2,3-b]pyridine and 300 mg of N4-(2-chlorophenyl)-6-iodo-N4-(2-methoxyethyl)pyrimidine-2,4-diamine are dissolved in 10 ml of methanol, and 780 mg of caesium carbonate are added. This mixture is degassed in vacuo using nitrogen. 95 mg of tetrakis(triphenylphosphine)palladium(0) are subsequently added, and the mixture is stirred at 100° C. in a sealed vessel for 3 h. When the reaction is complete, the batch is partitioned between water and ethyl acetate, the organic phase is dried over sodium sulfate, filtered and evaporated. The purification is carried out via preparative HPLC. The product fractions are combined and evaporated, giving 20 mg (5%) of the title compound; Rt: 1.759 min.; M+H$^+$: 470.10.

The compound inhibits the target protein in the enzymatic PDK1 inhibition assay with an IC$_{50}$ of 9.1 nM and PKB phosphorylation at Thr 308 in PC3 cells with an IC$_{50}$ of 53 nM.

The following compounds are obtained analogously

| No. | Structure/name | enzymatic IC$_{50}$ [nM] | cellular IC$_{50}$ [nM] | LC-MS; rt; [M + H$^+$]* |
|---|---|---|---|---|
| "A1" | N4-(3-Fluorophenyl)-N4-methyl-6-[5-(1-methyl-1H-pyrazol-4-yl)-1H-pyrrolo[2,3-b]pyridin-3-yl]pyrimidine-2,4-diamine<br>$^1$H NMR (400 MHz, DMSO-d$_6$) δ [ppm] 11.93 (s, 1H), 8.68 (d, J = 2.2, 1H), 8.50 (d, J = 2.1, 1H), 8.17 (d, J = 10.1, 1H), 8.02 (s, 1H), 7.93 (d, J = 0.6, 1H), 7.51 (dd, J = 15.1, 8.1, 1H), 7.33-7.21 (m, 2H), 7.20-7.07 (m, 1H), 6.25 (s, 1H), 6.22 (s, 2H), 3.92 (s, 3H), 3.42 (s, 3H) | 34 | 280 | 1.668 min [415.10] |
| "A2" | 4-(1-Methyl-1-phenylethyl)-6-[5-(1-methyl-1H-pyrazol-4-yl)-1H-pyrrolo-[2,3-b]pyridin-3-yl]pyrimidin-2-yl-amine | 65 | 140 | 1.751 min [410.20] |

-continued

| No. | Structure/name | enzymatic IC$_{50}$ [nM] | cellular IC$_{50}$ [nM] | LC-MS; rt; [M + H$^+$]* |
|---|---|---|---|---|
| "A3" | 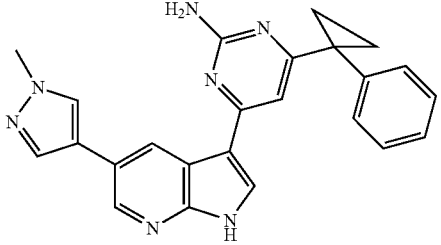 [SMILES: Cn1cc(-c2cnc3[nH]cc(-c4cc(C5(c6ccccc6)CC5)nc(N)n4)c3c2)cn1]

4-[5-(1-Methyl-1H-pyrazol-4-yl)-1H-pyrrolo[2,3-b]pyridin-3-yl]-6-(1-phenylcyclopropyl)pyrimidin-2-yl-amine | 59.5 | 110 | 1.816 min [408.10] |
| "A4" | 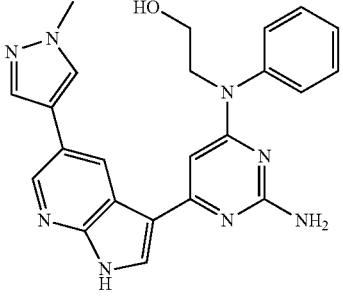 [SMILES: Cn1cc(-c2cnc3[nH]cc(-c4cc(N(CCO)c5ccccc5)nc(N)n4)c3c2)cn1]

2-({2-Amino-6-[5-(1-methyl-1H-pyrazol-4-yl)-1H-pyrrolo[2,3-b]-pyridin-3-yl]pyrimidin-4-yl}phenyl-amino)ethanol | 13 | 250 | 1.513 min [427.10] |

$^1$H NMR (400 MHz, DMSO-d$_6$) δ [ppm] 11.91 (s, 1H), 8.47 (d, J = 2.1, 1H), 8.37 (s, 1H), 8.13 (s, 1H), 8.06 (s, 1H), 7.83 (d, J = 2.2, 2H), 7.52 (t, J = 7.7, 2H), 7.45-7.40 (m, 2H), 7.37 (t, J = 7.3, 1H), 6.16 (s, 2H), 5.90 (s, 1H), 3.98 (t, J = 6.5, 2H), 3.92 (s, 3H), 3.63 (t, J = 6.5, 2H)

| "A5" | 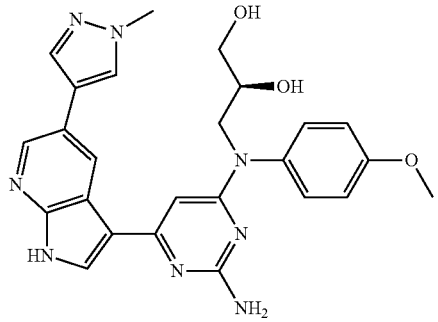 [SMILES: COc1ccc(N(C[C@H](O)CO)c2cc(-c3c[nH]c4ncc(-c5cnn(C)c5)cc34)nc(N)n2)cc1]

(S)-3-[{2-Amino-6-[5-(1-methyl-1H-pyrazol-4-yl)-1H-pyrrolo[2,3-b]-pyridin-3-yl]pyrimidin-4-yl}-(4-methoxyphenyl)amino]propane-1,2-diol | 24 | 6800 | 1.516 min [487.20] |

$^1$H NMR (400 MHz, DMSO-d$_6$) δ [ppm] 11.97 (s, 1H), 8.47 (d, J = 2.0, 1H), 8.28 (s, 1H), 8.13 (s, 1H), 8.05 (s, 1H), 7.83 (d, J = 8.1, 2H), 7.34 (d, J = 8.8, 2H), 7.07 (d, J = 8.9, 2H), 6.21 (s, 2H), 5.82 (s, 1H), 4.57 (s, 1H), 3.93 (d, J = 3H), 3.81 (s, 3H), 3.40 (d, J = 5.1, 2H)

-continued

| No. | Structure/name | enzymatic IC$_{50}$ [nM] | cellular IC$_{50}$ [nM] | LC-MS; rt; [M + H$^+$]* |
|---|---|---|---|---|
| "A6" | 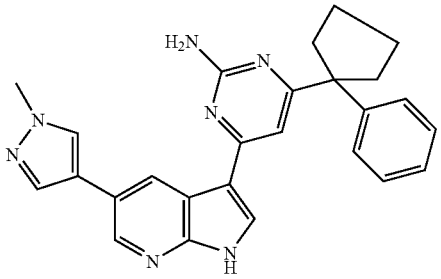 [SMILES: Cn1cc(-c2cnc3[nH]cc(-c4cc(C5(c6ccccc6)CCCC5)nc(N)n4)c3c2)cn1]<br>4-[5-(1-Methyl-1H-pyrazol-4-yl)-1H-pyrrolo[2,3-b]pyridin-3-yl]-6-(1-phenylcyclopentyl)pyrimidin-2-yl-amine | 130 | 625 | 1.839 min [436.20] |
| "A7" | 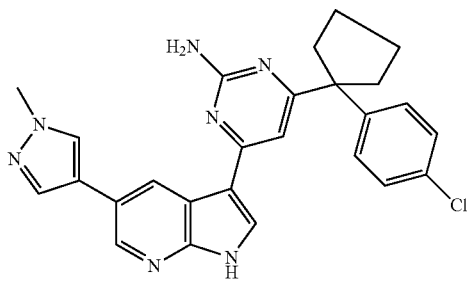 [SMILES: Cn1cc(-c2cnc3[nH]cc(-c4cc(C5(c6ccc(Cl)cc6)CCCC5)nc(N)n4)c3c2)cn1]<br>4-[1-(4-Chlorophenyl)cyclopentyl]-6-[5-(1-methyl-1H-pyrazol-4-yl)-1H-pyrrolo[2,3-b]pyridin-3-yl]pyrimidin-2-ylamine | 870 | 1400 | 1.960 min [470.15] |
| "A8" | 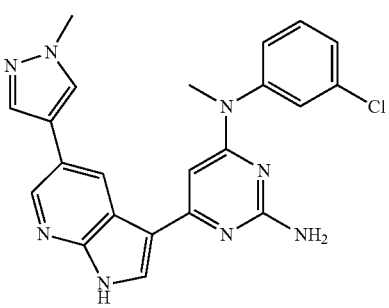 [SMILES: CN(c1cccc(Cl)c1)c1cc(-c2c[nH]c3ncc(-c4cnn(C)c4)cc23)nc(N)n1]<br>N4-(3-Chlorophenyl)-N4-methyl-6-[5-(1-methyl-1H-pyrazol-4-yl)-1H-pyrrolo[2,3-b]pyridin-3-yl]pyrimidine-2,4-diamine | 51 | 200 | 1.672 min [431.10] Schmelzpunkt: 264.0-265.5° C. |

$^1$H NMR (400 MHz, DMSO-d$_6$) δ [ppm] 11.95 (s, 1H), 8.71 (d, J = 2.1, 1H), 8.51 (d, J = 2.2, 1H), 8.16 (d, J = 6.1, 2H), 8.04 (d, J = 2.8, 1H), 7.95 (d, J = 0.6, 1H), 7.51 (d, J = 8.0, 1H), 7.49-7.47 (m, 1H), 7.36 (m, 2H), 6.24 (d, J = 4.5, 3H), 3.92 (s, 3H), 3.42 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A9" | 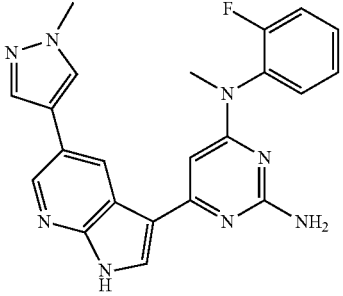 [SMILES: CN(c1cc(-c2c[nH]c3ncc(-c4cnn(C)c4)cc23)nc(N)n1)c1ccccc1F]<br>N4-(2-Fluorophenyl)-N4-methyl-6-[5-(1-methyl-1H-pyrazol-4-yl)-1H-pyrrolo[2,3-b]pyridin-3-yl]pyrimidine-2,4-diamine | 9.7 | 27 | 1.592 min [415.10] Schmelz-punkt: 324.0-326.0° C. |

$^1$H NMR (400 MHz, DMSO-d$_6$) δ [ppm] 11.93 (s, 1H), 8.64 (d, J = 2.0, 1H), 8.49 (d, J = 2.1, 1H), 8.13 (s, 2H), 8.00 (d, J = 2.8, 1H), 7.91 (s, 1H), 7.49 (m, 1H), 7.37 (m, 3H), 6.18 (s, 2H), 6.07 (s, 1H), 3.91 (s, 3H), 3.35 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A10" | 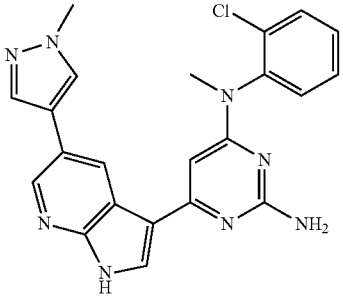 [SMILES: CN(c1cc(-c2c[nH]c3ncc(-c4cnn(C)c4)cc23)nc(N)n1)c1ccccc1Cl]<br>N4-(2-Chlorophenyl)-N4-methyl-6-[5-(1-methyl-1H-pyrazol-4-yl)-1H-pyrrolo[2,3-b]pyridin-3-yl]pyrimidine-2,4-diamine | 7.6 | 26 | 1.661 min [431.10] |

$^1$H NMR (400 MHz, DMSO-d$_6$) δ [ppm] 11.76 (s, 1H), 8.56 (dd, J = 13.1, 2.2, 1H), 8.51 (dd, J = 6.1, 2.1, 1H), 8.19-8.10 (m, 1H), 7.94 (d, J = 23.6, 2H), 7.67 (d, J = 7.8, 1H), 7.52 (t, J = 6.5, 2H), 7.45 (t, J = 13.5, 1H), 6.29-6.13 (m, 2H), 3.91 (s, 3H), 3.45 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A11" | 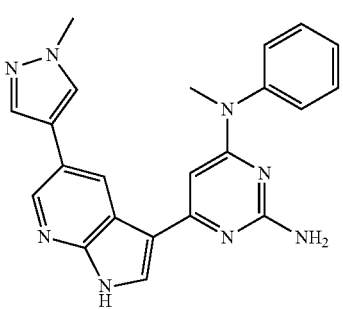 [SMILES: CN(c1ccccc1)c1cc(-c2c[nH]c3ncc(-c4cnn(C)c4)cc23)nc(N)n1]<br>N4-Methyl-6-[5-(1-methyl-1H-pyrazol-4-yl)-1H-pyrrolo[2,3-b]-pyridin-3-yl]-N4-phenylpyrimidine-2,4-diamine | 16.5 | 800 | 1.631 min [397.10] |

$^1$H NMR (400 MHz, DMSO-d$_6$) δ [ppm] 11.98 (s, 1H), 8.54-8.47 (m, 2H), 8.20-8.09 (m, 2H), 7.96-7.86 (m, 2H), 7.52 (t, J = 7.8, 2H), 7.40 (d, J = 7.4, 2H), 7.34 (t, J = 7.4, 1H), 6.22 (s, 2H), 6.10 (s, 1H), 3.92 (s, 3H), 3.45 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A12" | N4-Ethyl-6-[5-(1-methyl-1H-pyrazol-4-yl)-1H-pyrrolo[2,3-b]pyridin-3-yl]-N4-phenylpyrimidine-2,4-diamine | 12 | 690 | 1.688 min [411.20] |

$^1$H NMR (400 MHz, DMSO-d$_6$) δ [ppm] 11.91 (s, 1H), 8.48 (d, J = 2.1, 1H), 8.41 (d, J = 2.1, 1H), 8.08 (s, 1H), 7.85 (dd, J = 5.7, 1.5, 2H), 7.54 (t, J = 7.7, 2H), 7.42-7.34 (m, 3H), 6.15 (s, 2H), 5.89 (s, 1H), 3.97 (q, J = 7.0, 2H), 3.92 (s, 3H), 1.12 (q, J = 7.0, 3H)

| No. | Structure/name | enzymatic IC$_{50}$ [nM] | cellular IC$_{50}$ [nM] | LC-MS; rt; [M + H$^+$]* |
|---|---|---|---|---|
| "A13" | N4-(4-Chlorophenyl)-N4-ethyl-6-[5-(1-methyl-1H-pyrazol-4-yl)-1H-pyrrolo[2,3-b]pyridin-3-yl]pyrimidine-2,4-diamine | 46 | 120 | 1.748 min [445.10] |

$^1$H NMR (400 MHz, DMSO-d$_6$) δ [ppm] 11.94 (s, 1H), 8.60 (d, J = 2.1, 1H), 8.49 (d, J = 2.1, 1H), 8.14 (s, 1H), 7.99-7.90 (m, 2H), 7.59-7.51 (m, 2H), 7.43-7.35 (m, 2H), 7.24 (d, J = 7.0, 1H), 7.09 (t, J = 7.5, 1H), 6.20 (s, 2H), 5.99 (s, 1H), 3.95 (q, J = 7.2, 2H), 3.92 (s, 3H), 1.12 (t, J = 7.0, 3H).

| No. | Structure/name | enzymatic IC$_{50}$ [nM] | cellular IC$_{50}$ [nM] | LC-MS; rt; [M + H$^+$]* |
|---|---|---|---|---|
| "A14" | N4-Benzyl-N4-ethyl-6-[5-(1-methyl-1H-pyrazol-4-yl)-1H-pyrrolo[2,3-b]-pyridin-3-yl]pyrimidine-2,4-diamine | 51 | 530 | 1.757 min [425.20] |

$^1$H NMR (400 MHz, DMSO-d$_6$) δ [ppm] 11.99 (s, 1H), 8.80 (s, 1H), 8.51 (d, J = 2.1, 1H), 8.18 (s, 2H), 7.97 (s, 1H), 7.38-7.27 (m, 4H), 7.27-7.20 (m, 1H), 6.41 (s, 1H), 6.23 (s, 1H), 4.81 (s, 2H), 3.90 (s, 3H), 3.55 (q, J = 6.3, 2H), 1.13 (t, J = 7.0, 3H)

| No. | Structure/name | enzymatic IC$_{50}$ [nM] | cellular IC$_{50}$ [nM] | LC-MS; rt; [M + H$^+$]* |
|---|---|---|---|---|
| "A15" | 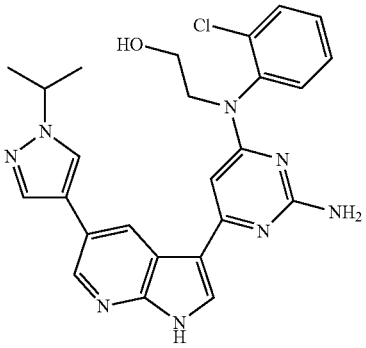 [SMILES: CC(C)n1cc(-c2cnc3[nH]cc(-c4cc(N(CCO)c5ccccc5Cl)nc(N)n4)c3c2)cn1]<br>2-[{2-Amino-6-[5-(1-isopropyl-1H-pyrazol-4-yl)-1H-pyrrolo[2,3-b]-pyridin-3-yl]pyrimidin-4-yl}-(2-chloro-phenyl)amino]ethanol | 17 | 2100 | 1.749 min [489.20] |
| "A16" | 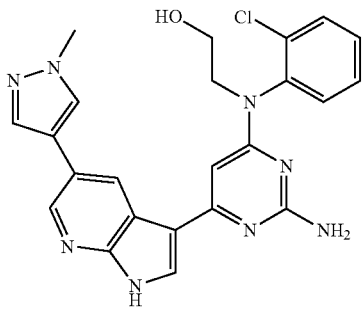 [SMILES: Cn1cc(-c2cnc3[nH]cc(-c4cc(N(CCO)c5ccccc5Cl)nc(N)n4)c3c2)cn1]<br>2-[{2-Amino-6-[5-(1-methyl-1H-pyrazol-4-yl)-1H-pyrrolo[2,3-b]-pyridin-3-yl]pyrimidin-4-yl}-(2-chloro-phenyl)amino]ethanol<br>$^1$H NMR (400 MHz, DMSO-d$_6$) δ [ppm] 11.93 (s, 1H), 8.48 (d, J = 2.0, 1H), 8.14 (s, 1H), 8.09 (s, 1H), 7.95-7.81 (m, 2H), 7.68 (d, J = 7.8, 1H), 7.62-7.56 (m, 1H), 7.52 (t, J = 7.3, 1H), 7.46 (t, J = 7.4, 1H), 6.18 (s, 2H), 5.88-5.45 (m, 1H), 3.92 (s, 3H) | 4.7 | 2.6 | 1.576 min [461.10] |
| "A17" | 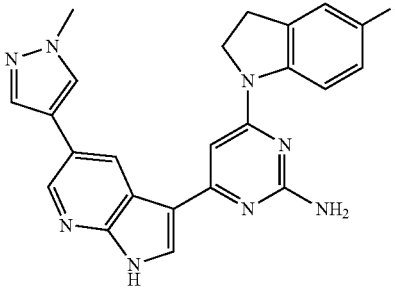<br>4-(5-Fluoro-2,3-dihydroindol-1-yl)-6-[5-(1-methyl-1H-pyrazol-4-yl)-1H-pyrrolo[2,3-b]pyridin-3-yl]pyrimidin-2-ylamine<br>$^1$H NMR (400 MHz, DMSO-d$_6$) δ [ppm] 11.95 (s, 0H), 9.03 (d, J = 2.2, 1H), 8.60 (dd, J = 8.9, 5.1, 1H), 8.54 (d, J = 2.2, 1H), 8.32 (s, 1H), 8.27 (s, 1H), 8.06 (s, 1H), 7.08 (dd, J = 8.5, 2.6, 1H), 6.93 (td, J = 9.1, 2.8, 1H), 6.49 (s, 1H), 6.42 (s, 2H), 4.12 (t, J = 8.7, 2H), 3.93 (s, 3H), 3.23 (t, J = 8.6, 4H) | 200 | >10000 | 1.772 min [427.15] |

| No. | Structure/name | enzymatic IC$_{50}$ [nM] | cellular IC$_{50}$ [nM] | LC-MS; rt; [M + H$^+$]* |
|---|---|---|---|---|
| "A18" | 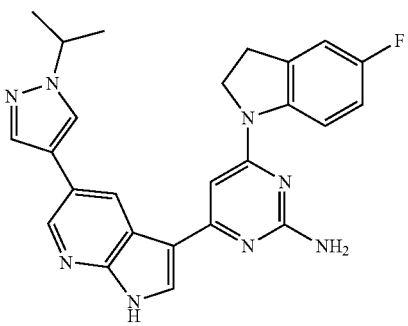 [SMILES: CC(C)n1cc(-c2cnc3[nH]cc(-c4cc(N5CCc6cc(F)ccc65)nc(N)n4)c3c2)cn1]<br>4-(5-Fluoro-2,3-dihydroindol-1-yl)-6-[5-(1-isopropyl-1H-pyrazol-4-yl)-1H-pyrrolo[2,3-b]pyridin-3-yl]pyrimidin-2-ylamine | 5900 | >10000 | 1.905 min [455.20] |

$^1$H NMR (400 MHz, DMSO-d$_6$) δ [ppm] 12.00 (d, J = 1.8, 1H), 9.03 (d, J = 2.0, 1H), 8.59 (dd, J = 8.9, 5.1, 1H), 8.55 (d, J = 2.2, 1H), 8.33-8.29 (m, 2H), 8.13 (s, 1H), 8.04 (d, J = 4.6, 1H), 7.07 (dd, J = 8.5, 2.6, 1H), 6.91 (td, J = 9.0, 2.7, 1H), 6.48 (s, 1H), 6.42 (s, 2H), 4.54 (hept, J = 6.7, 1H), 4.18-4.04 (m, 2H), 3.22 (t, J = 8.6, 2H), 1.50 (d, J = 6.7, 6H)

| No. | Structure/name | enzymatic IC$_{50}$ [nM] | cellular IC$_{50}$ [nM] | LC-MS; rt; [M + H$^+$]* |
|---|---|---|---|---|
| "A19" | 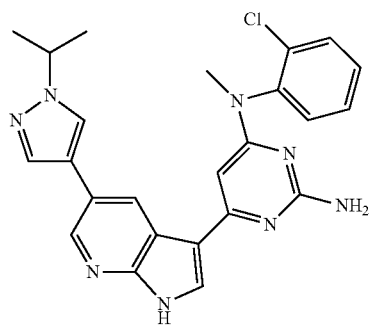 [SMILES: CC(C)n1cc(-c2cnc3[nH]cc(-c4cc(N(C)c5ccccc5Cl)nc(N)n4)c3c2)cn1]<br>N4-(2-Chlorophenyl)-6-[5-(1-isopropyl-1H-pyrazol-4-yl)-1H-pyrrolo[2,3-b]pyridin-3-yl]-N4-methyl-pyrimidine-2,4-diamine | 30 | 400 | 1.841 min [459.15] |

$^1$H NMR (400 MHz, DMSO-d$_6$) δ [ppm] 11.90 (s, 1H), 8.56 (d, J = 7.5, 1H), 8.51 (d, J = 2.0, 1H), 8.20 (s, 1H), 8.14 (s, 1H), 7.88 (s, 1H), 7.65 (d, J = 7.4, 1H), 7.50 (dd, J = 8.3, 5.1, 2H), 7.46-7.39 (m, 1H), 6.17 (s, 2H), 5.86 (s, 1H), 4.55 (hept, J = 6.7, 1H), 1.49 (d, J = 6.7, 6H)

| No. | Structure/name | enzymatic IC$_{50}$ [nM] | cellular IC$_{50}$ [nM] | LC-MS; rt; [M + H$^+$]* |
|---|---|---|---|---|
| "A20" | 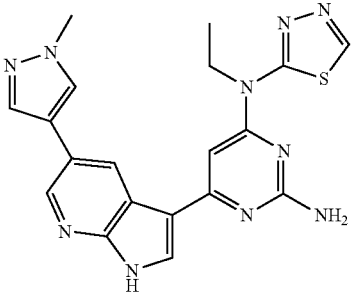 [SMILES: CCN(c1cc(-c2c[nH]c3ncc(-c4cnn(C)c4)cc23)nc(N)n1)c1nncs1]<br>N4-Ethyl-6-[5-(1-methyl-1H-pyrazol-4-yl)-1H-pyrrolo[2,3-b]pyridin-3-yl]-N4-1,3,4-thiadiazol-2-ylpyrimidine-2,4-diamine | 155 | >10000 | 1.728 min [419.10] |

$^1$H NMR (400 MHz, DMSO-d$_6$) δ [ppm] 12.15 (s, 1H), 9.10 (d, J = 34.0, 2H), 8.55 (s, 2H), 8.26 (s, 1H), 8.17 (s, 0H), 8.07 (s, 1H), 6.97 (s, 1H), 6.78 (s, 2H), 4.48 (d, J = 5.5, 2H), 3.91 (s, 3H), 1.34 (s, 3H)

-continued

| No. | Structure/name | enzymatic IC$_{50}$ [nM] | cellular IC$_{50}$ [nM] | LC-MS; rt; [M + H$^+$]* |
|---|---|---|---|---|
| "A21" | 1-({2-Amino-6-[5-(1-methyl-1H-pyrazol-4-yl)-1H-pyrrolo[2,3-b]-pyridin-3-yl]pyrimidin-4-yl}phenyl-amino)-3-methoxypropan-2-ol | 11 | 520 | 1.644 min [471.20] |

$^1$H NMR (400 MHz, DMSO-d$_6$) δ [ppm] 11.93 (s, 1H), 8.47 (dd, J = 14.5, 2.1, 1H), 8.38 (d, J = 2.0, 1H), 8.08 (s, 1H), 7.88-7.80 (m, 2H), 7.52 (t, J = 7.8, 2H), 7.45-7.41 (m, 2H), 7.37 (t, J = 7.4, 1H), 6.17 (d, J = 13.5, 2H), 5.92 (s, 1H), 4.01 (dd, J = 13.7, 4.6, 1H), 3.97-3.93 (m, 1H), 3.93 (s, 3H), 3.86 (dd, J = 13.7, 7.2, 1H), 3.33-3.27 (m, 2H), 3.20 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A22" | 3-[{2-Amino-6-[5-(1-methyl-1H-pyrazol-4-yl)-1H-pyrrolo[2,3-b]-pyridin-3-yl]pyrimidin-4-yl}-(2,3-dihydroxypropyl)amino]benzonitrile | 90 | >10000 | 1.549 min [482.20] |
| "A23" | 3-[{2-Amino-6-[5-(1-methyl-1H-pyrazol-4-yl)-1H-pyrrolo[2,3-b]-pyridin-3-yl]pyrimidin-4-yl}-(2-chloro-phenyl)amino]propionic acid | 4.8 | >10000 | 1700 min [489.15] |

-continued

| No. | Structure/name | enzymatic IC$_{50}$ [nM] | cellular IC$_{50}$ [nM] | LC-MS; rt; [M + H$^+$]* |
|---|---|---|---|---|
| "A24" | Methyl [{2-amino-6-[5-(1-methyl-1H-pyrazol-4-yl)-1H-pyrrolo[2,3-b]-pyridin-3-yl]pyrimidin-4-yl}-(4-chlorophenyl)amino]acetate | 69 | 470 | 1.810 min [489.10] |

$^1$H NMR (400 MHz, DMSO-d$_6$) δ [ppm] 11.95 (s, 1H), 8.60 (d, J = 2.0, 1H), 8.49 (d, J = 2.1, 1H), 8.14 (s, 2H), 7.97 (dd, J = 7.8, 2.9, 1H), 7.92 (s, 1H), 7.56 (d, J = 8.7, 2H), 7.46 (d, J = 8.7, 2H), 6.25 (s, 2H), 6.08 (s, 1H), 4.68 (s, 2H), 3.91 (s, 3H), 3.66 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A25" | 2-[{2-Amino-6-[5-(1-methyl-1H-pyrazol-4-yl)-1H-pyrrolo[2,3-b]-pyridin-3-yl]pyrimidin-4-yl}-(2,4-difluorophenyl)amino]ethanol | 6.5 | 35 | 1.648 min [463.10] |

$^1$H NMR (400 MHz, DMSO-d$_6$) δ [ppm] 11.95 (s, 1H), 8.63 (s, 1H), 8.49 (d, J = 1.9, 1H), 8.13 (s, 1H), 7.98 (d, J = 24.6, 1H), 7.92 (s, 1H), 7.67-7.54 (m, 2H), 7.50-7.38 (m, 1H), 7.22 (td, J = 8.4, 2.2, 1H), 6.20 (s, 2H), 5.95 (s, 1H), 4.73 (t, J = 5.0, 1H), 3.91 (s, 3H), 3.87 (s, 2H), 3.62 (dd, J = 11.6, 6.0, 2H)

| No. | Structure/name | enzymatic IC$_{50}$ [nM] | cellular IC$_{50}$ [nM] | LC-MS; rt; [M + H$^+$]* |
|---|---|---|---|---|
| "A26" | 2-[{2-Amino-6-[5-(1-methyl-1H-pyrazol-4-yl)-1H-pyrrolo[2,3-b]-pyridin-3-yl]pyrimidin-4-yl}-(2-fluorophenyl)amino]ethanol | 5 | 23 | 1.638 min [445.15] |

$^1$H NMR (400 MHz, DMSO-d$_6$) δ [ppm] 11.93 (s, 1H), 8.53 (s, 1H), 8.49 (d, J = 2.1, 1H), 8.11 (s, 1H), 7.92 (d, J = 2.5, 1H), 7.88 (s, 1H), 7.55 (td, J = 7.9, 1.5, 1H), 7.49-7.41 (m, 1H), 7.41-7.37 (m, 1H), 7.34 (dd, J = 11.9, 4.4, 1H), 6.16 (s, 2H), 5.92 (s, 1H), 4.72 (t, J = 5.3, 1H), 3.90 (s, 3H), 3.62 (dd, J = 12.0, 6.4, 2H)

-continued

| No. | Structure/name | enzymatic IC$_{50}$ [nM] | cellular IC$_{50}$ [nM] | LC-MS; rt; [M + H$^+$]* |
|---|---|---|---|---|
| "A27" | 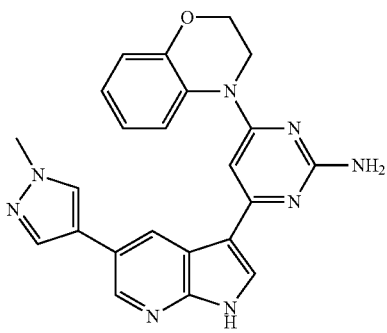 [SMILES: Cn1cc(-c2cnc3[nH]cc(-c4cc(N5CCOc6ccccc65)nc(N)n4)c3c2)cn1]<br>4-(2,3-Dihydrobenzo-1,4-oxazin-4-yl)-6-[5-(1-methyl-1H-pyrazol-4-yl)-1H-pyrrolo[2,3-b]pyridin-3-yl]-pyrimidin-2-ylamine | 5 | >10000 | 1.640 min [425.10] |
| "A28" | 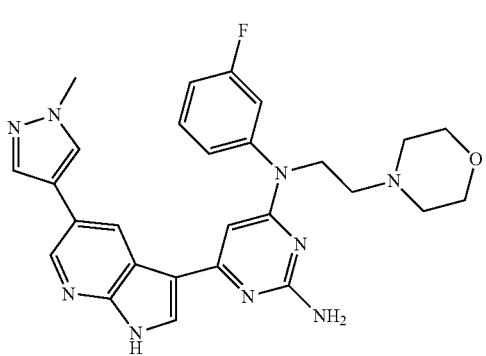 [SMILES: Cn1cc(-c2cnc3[nH]cc(-c4cc(N(CCN5CCOCC5)c5cccc(F)c5)nc(N)n4)c3c2)cn1]<br>N4-(3-Fluorophenyl)-6-[5-(1-methyl-1H-pyrazol-4-yl)-1H-pyrrolo[2,3-b]-pyridin-3-yl]-N4-(2-morpholin-4-yl-ethyl)pyrimidine-2,4-diamine | 89 | 9700 | 1.500 min [514.20] |
| "A29" | 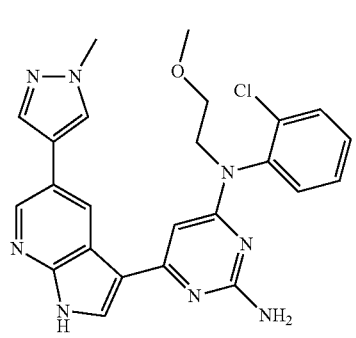 [SMILES: COCCN(c1cc(-c2c[nH]c3ncc(-c4cnn(C)c4)cc23)nc(N)n1)c1ccccc1Cl]<br>N4-(2-Chlorophenyl)-N4-(2-methoxy-ethyl)-6-[5-(1-methyl-1H-pyrazol-4-yl)-1H-pyrrolo[2,3-b]pyridin-3-yl]-pyrimidine-2,4-diamine | 7 | 25.5 | 1.754 min [475.15] |

$^1$H NMR (400 MHz, DMSO-d$_6$) δ [ppm] 11.89 (s, 1H), 8.48 (q, J = 2.9, 1H), 8.08 (d, J = 6.4, 1H), 7.89-7.83 (m, 1H), 7.68 (d, J = 7.8, 1H), 7.53 (d, J = 4.1, 2H), 7.50-7.43 (m, 1H), 7.42-7.36 (m, 1H), 6.25-6.06 (m, 2H), 5.96-5.84 (m, 0H), 3.97 (s, 3H), 3.63-3.48 (m, 2H), 3.21 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A30" | 3-({2-Amino-6-[5-(1-methyl-1H-pyrazol-4-yl)-1H-pyrrolo[2,3-b]-pyridin-3-yl]pyrimidin-4-yl}phenyl-amino)propionitrile | 7.9 | 7.1 | 1.725 min [436.20] |

$^1$H NMR (400 MHz, DMSO-d$_6$) δ [ppm] 12.67 (s, 1H), 12.47 (s, 1H), 8.62 (d, J = 27.7, 1H), 8.26 (d, J = 21.3, 1H), 8.03 (d, J = 37.6, 1H), 7.74-7.70 (m, 1H), 7.68 (d, J = 7.4, 2H), 7.59 (d, J = 5.7, 3H), 5.89 (s, 1H), 4.48-4.17 (m, 2H), 4.02-3.86 (m, 3H), 2.98 (t, J = 6.7, 2H)

| No. | Structure/name | enzymatic IC$_{50}$ [nM] | cellular IC$_{50}$ [nM] | LC-MS; rt; [M + H$^+$]* |
|---|---|---|---|---|
| "A30a" | (3-Fluorophenyl)methyl-{6-[5-(1-methyl-1H-pyrazol-4-yl)-1H-pyrrolo[2,3-b]pyridin-3-yl]pyrimidin-4-yl}amine | 190 | 660 | 1.653 min [400.10] |

$^1$H NMR (400 MHz, DMSO-d$_6$) δ [ppm] 12.18 (s, 1H), 8.64 (d, J = 1.0, 1H), 8.53 (d, J = 2.1, 1H), 8.48 (d, J = 2.1, 1H), 8.26 (s, 1H), 8.09 (s, 1H), 7.81 (d, J = 0.6, 1H), 7.56 (dd, J = 15.0, 8.1, 1H), 7.38 (dt, J = 10.5, 2.2, 1H), 7.31 (dd, J = 8.0, 1.2, 1H), 7.20 (td, J = 8.4, 1.9, 1H), 6.94 (d, J = 1.1, 1H), 3.92 (s, 3H), 3.50 (s, 3H)

| No. | Structure/name | enzymatic IC$_{50}$ [nM] | cellular IC$_{50}$ [nM] | LC-MS; rt; [M + H$^+$]* |
|---|---|---|---|---|
| "A31" | N4-(3-Aminopropyl)-6-[5-(1-methyl-1H-pyrazol-4-yl)-1H-pyrrolo[2,3-b]-pyridin-3-yl]-N4-phenylpyrimidine-2,4-diamine | 8.7 | 6800 | |

| No. | Structure/name | enzymatic IC$_{50}$ [nM] | cellular IC$_{50}$ [nM] | LC-MS; rt; [M + H$^+$]* |
|---|---|---|---|---|
| "A32" | N4-(3-Aminopropyl)-6-[5-(1-methyl-1H-pyrazol-4-yl)-1H-pyrrolo[2,3-b]-pyridin-3-yl]-N4-(2-methylpyridin-4-yl)pyrimidine-2,4-diamine | | | |
| "A33" | 3-[{2-Amino-6-[5-(1-methyl-1H-pyrazol-4-yl)-1H-pyrrolo[2,3-b]-pyridin-3-yl]pyrimidin-4-yl}-(2-methylpyridin-4-yl)amino]-propionitrile | | | |
| "A34" | 4-[5-(1-Methyl-1H-pyrazol-4-yl)-1H-pyrrolo[2,3-b]pyridin-3-yl]-6-[1-(2-methylpyridin-4-yl)cyclopropyl]-pyrimidin-2-ylamine | | | |

| No. | Structure/name | enzymatic IC$_{50}$ [nM] | cellular IC$_{50}$ [nM] | LC-MS; rt; [M + H$^+$]* |
|---|---|---|---|---|
| "A35" | 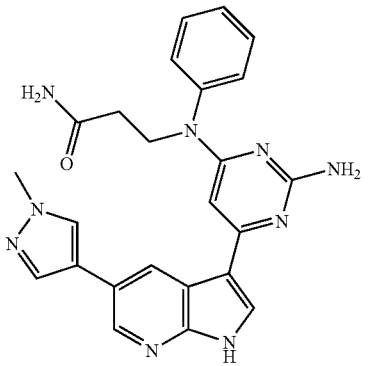 [SMILES: Cn1cc(-c2cnc3[nH]cc(-c4cc(N(CCC(N)=O)c5ccccc5)nc(N)n4)c3c2)cn1]<br>3-({2-Amino-6-[5-(1-methyl-1H-pyrazol-4-yl)-1H-pyrrolo[2,3-b]-pyridin-3-yl]pyrimidin-4-yl}phenyl-amino)propionamide | 17 | 23000 | |
| "A36" | 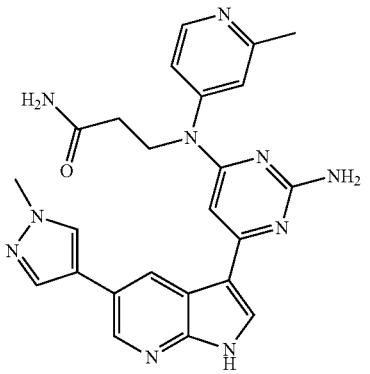 [SMILES: Cc1cc(N(CCC(N)=O)c2cc(-c3c[nH]c4ncc(-c5cnn(C)c5)cc34)nc(N)n2)ccn1]<br>3-[{2-Amino-6-[5-(1-methyl-1H-pyrazol-4-yl)-1H-pyrrolo[2,3-b]-pyridin-3-yl]pyrimidin-4-yl}-(2-methylpyridin-4-yl)amino]-propionamide | | | |
| "A37" | 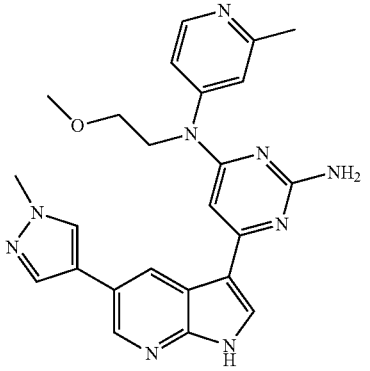 [SMILES: COCCN(c1ccnc(C)c1)c1cc(-c2c[nH]c3ncc(-c4cnn(C)c4)cc23)nc(N)n1]<br>N4-(2-Methoxyethyl)-6-[5-(1-methyl-1H-pyrazol-4-yl)-1H-pyrrolo[2,3-b]pyridin-3-yl]-N4-(2-methylpyridin-4-yl)pyrimidine-2,4-diamine | | | |

| No. | Structure/name | enzymatic IC$_{50}$ [nM] | cellular IC$_{50}$ [nM] | LC-MS; rt; [M + H$^+$]* |
|---|---|---|---|---|
| "A38" | 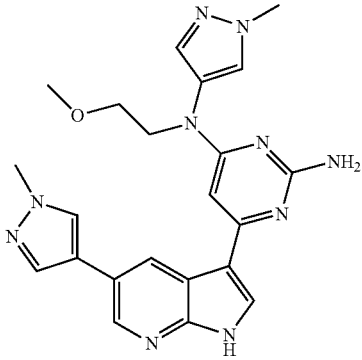 [SMILES: COCCN(c1cnn(C)c1)c1cc(-c2c[nH]c3ncc(-c4cnn(C)c4)cc23)nc(N)n1]<br>N4-(2-Methoxyethyl)-6-[5-(1-methyl-1H-pyrazol-4-yl)-1H-pyrrolo[2,3-b]pyridin-3-yl]-N4-(1-methylpyrazol-4-yl)pyrimidine-2,4-diamine | | | |
| "A39" | 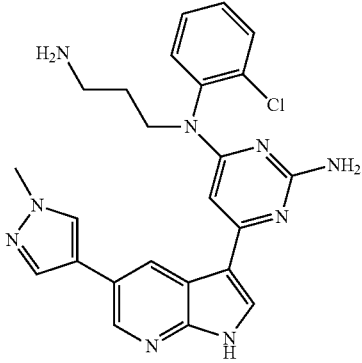 [SMILES: Cn1cc(-c2cnc3[nH]cc(-c4cc(N(CCCN)c5ccccc5Cl)nc(N)n4)c3c2)cn1]<br>N4-(3-Aminopropyl)-6-[5-(1-methyl-1H-pyrazol-4-yl)-1H-pyrrolo[2,3-b]-pyridin-3-yl]-N4-(2-chlorophenyl)-pyrimidine-2,4-diamine | | | |
| "A40" | 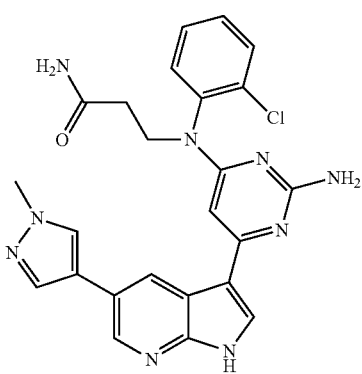 [SMILES: Cn1cc(-c2cnc3[nH]cc(-c4cc(N(CCC(N)=O)c5ccccc5Cl)nc(N)n4)c3c2)cn1]<br>3-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]propionamide | | | |

| No. | Structure/name | enzymatic IC$_{50}$ [nM] | cellular IC$_{50}$ [nM] | LC-MS; rt; [M + H$^+$]* |
|---|---|---|---|---|
| "A41" | 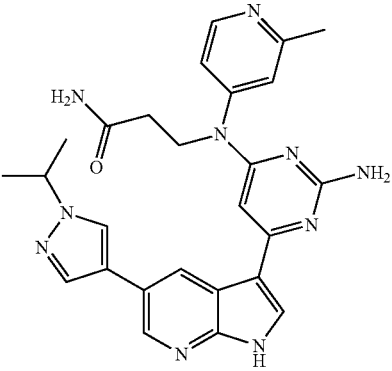 [SMILES: Cc1cc(N(CCC(N)=O)c2cc(-c3c[nH]c4ncc(-c5cnn(C(C)C)c5)cc34)nc(N)n2)ccn1]<br>3-[{2-Amino-6-[5-(1-isopropyl-1H-pyrazol-4-yl)-1H-pyrrolo[2,3-b]-pyridin-3-yl]pyrimidin-4-yl}-(2-methylpyridin-4-yl)amino]-propionamide | | | |
| "A42" | 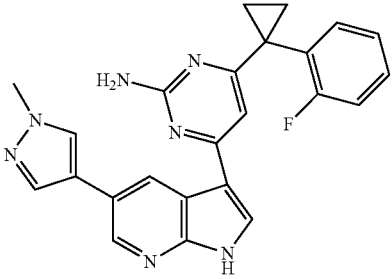 [SMILES: Cn1cc(-c2cnc3[nH]cc(-c4cc(C5(c6ccccc6F)CC5)nc(N)n4)c3c2)cn1]<br>4-[1-(2-Fluorophenyl)cyclopropyl]-6-[5-(1-methyl-1H-pyrazol-4-yl)-1H-pyrrolo[2,3-b]pyridin-3-yl]pyrimidin-2-ylamine | 45.5 | 20 | |
| "A43" | 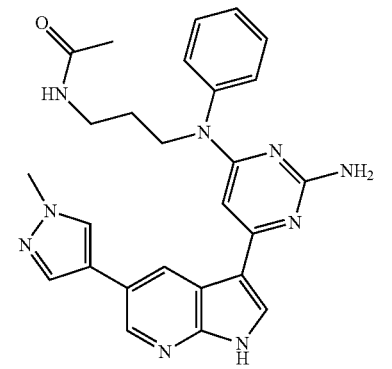 [SMILES: CC(=O)NCCCN(c1ccccc1)c1cc(-c2c[nH]c3ncc(-c4cnn(C)c4)cc23)nc(N)n1]<br>N-[3-({2-Amino-6-[5-(1-methyl-1H-pyrazol-4-yl)-1H-pyrrolo[2,3-b]-pyridin-3-yl]pyrimidin-4-yl}phenyl-amino)propyl]acetamide | 22 | 430 | |

TABLE I
Comparison of compounds from WO 2010/000364 and compounds according to the invention*
| | | PDK1 inhibition assay enzymatic IC$_{50}$ [nM] | PDK1 inhibition assay cellular IC$_{50}$ [nM] |
|---|---|---|---|
| 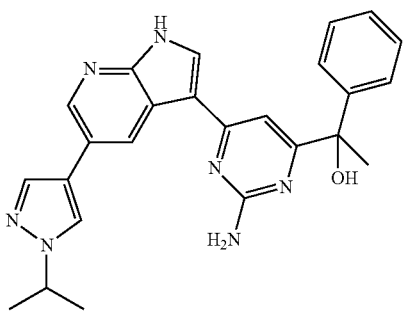 WO 2010/000364 "A55" | Solubility <1 µg/ml | 54 | 492 |
| 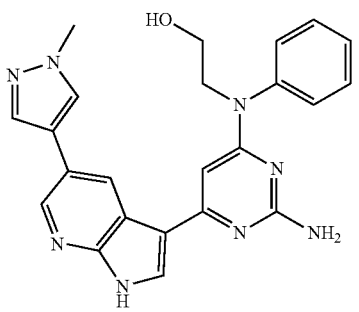 "A4"* | Solubility 1 µg/ml | 13 | 250 |
| 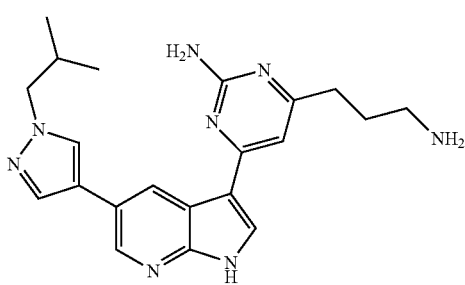 WO 2010/000364 | | 11 | >30 µM |
| 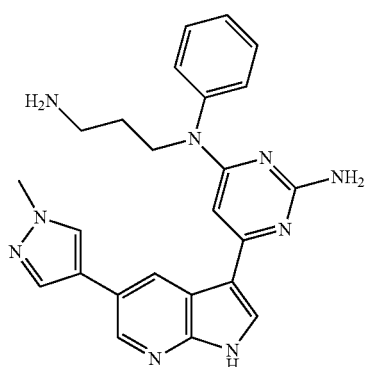 "A31"* | | 8.7 | 6.8 µM |

TABLE I-continued
Comparison of compounds from WO 2010/000364 and compounds according to the invention*
| | | PDK1 inhibition assay enzymatic IC$_{50}$ [nM] | PDK1 inhibition assay cellular IC$_{50}$ [nM] |
|---|---|---|---|
| 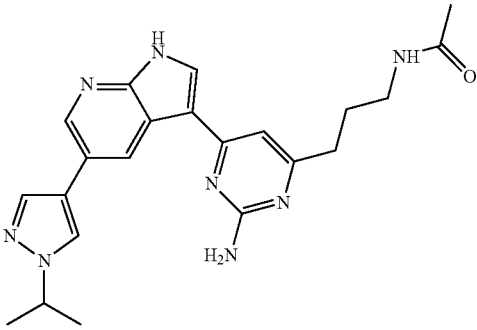 WO 2010/000364 | Solubility >46 µg/ml | 240 | >30 µM |
| 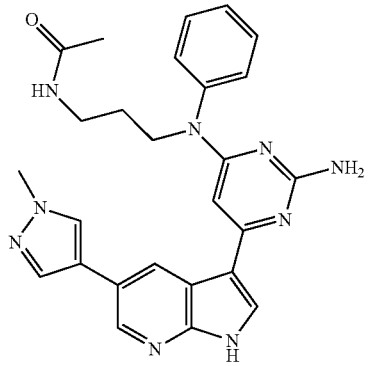 "A43"* | | 22 | 430 nM |
| 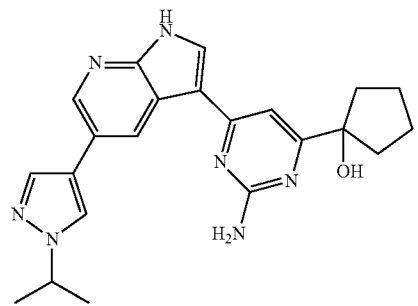 WO 2010/000364 | Solubility 8 µg/ml | 61 | 3.5 µM |
| 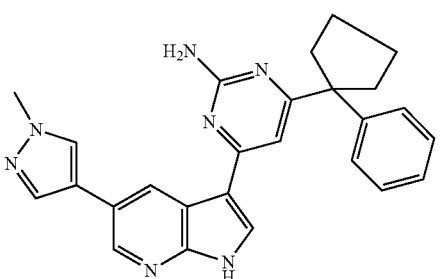 "A6"* | Solubility <1 µg/ml | 130 | 0.625 µM |

The following examples relate to medicaments:

Example A

Injection Vials

A solution of 100 g of an active compound according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active compound.

Example B

Suppositories

A mixture of 20 g of an active compound according to the invention with 100 g of soya lecithin and 1400 g of cocoa butter is melted, poured into moulds and allowed to cool. Each suppository contains 20 mg of active compound.

Example C

Solution

A solution is prepared from 1 g of an active compound according to the invention, 9.38 g of $NaH_2PO_4.2H_2O$, 28.48 g of $Na_2HPO_4.12 H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active compound according to the invention are mixed with 99.5 g of Vaseline under aseptic conditions.

Example E

Tablets

A mixture of 1 kg of active compound, 4 kg of lactose, 1.2 kg of potato starch, 0.2 kg of talc and 0.1 kg of magnesium stearate is pressed in a conventional manner to give tablets in such a way that each tablet contains 10 mg of active compound.

Example F

Dragees

Tablets are pressed analogously to Example E and subsequently coated in a conventional manner with a coating of sucrose, potato starch, talc, tragacanth and dye.

Example G

Capsules 2 kg of active compound are introduced into hard gelatine capsules in a conventional manner in such a way that each capsule contains 20 mg of the active compound.

Example H

Ampoules

A solution of 1 kg of active compound in 60 l of bidistilled water is sterile filtered, transferred into ampoules, lyophilised under sterile conditions and sealed under sterile conditions. Each ampoule contains 10 mg of active compound.

---

The invention claimed is:

1. A method for the treatment of a tumour, tumour growth, or tumour metastases, where the tumour originates from a tumour of the squamous epithelium, of the bladder, of the kidneys, of the head and neck, of the oesophagus, of the cervix, of the thyroid, of the intestine, of the liver, of the brain, of the prostate, of the urogenital tract, of the lymphatic system, of the stomach, of the larynx or of the lung or originates from monocytic leukaemia, lung adenocarcinoma, small-cell lung carcinoma, pancreatic cancer, colon carcinoma, glioblastoma or breast carcinoma, comprising administering to a subject in need thereof an effective amount of one of the following compounds

| No. | Structure/name |
|---|---|
| "A1" | 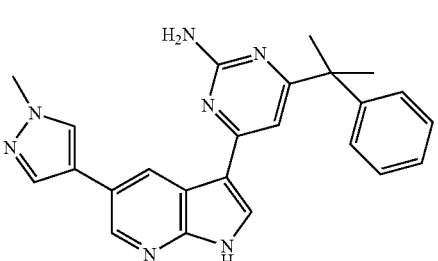<br>N4-(3-Fluorophenyl)-N4-methyl-6-[5-(1-methyl-1H-pyrazol-4-yl)-1H-pyrrolo[2,3-b]pyridin-3-yl]pyrimidine-2,4-diamine |
| "A2" | 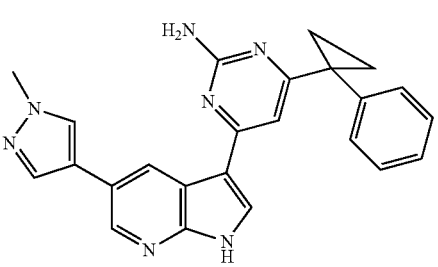<br>4-(1-Methyl-1-phenylethyl)-6-[5-(1-methyl-1H-pyrazol-4-yl)-1H-pyrrolo[2,3-b]pyridin-3-yl]pyrimidin-2-ylamine |
| "A3" | 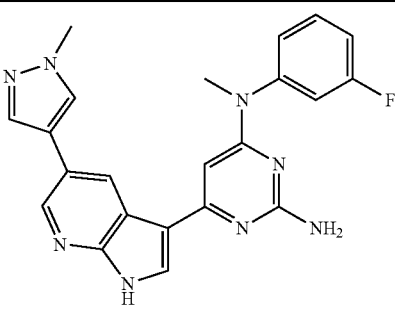<br>4-[5-(1-Methyl-1H-pyrazol-4-yl)-1H-pyrrolo[2,3-b]pyridin-3-yl]-6-(1-phenylcyclopropyl)pyrimidin-2-ylamine |

| No. | Structure/name |
|---|---|
| "A4" | 2-({2-Amino-6-[5-(1-methyl-1H-pyrazol-4-yl)-1H-pyrrolo[2,3-b]-pyridin-3-yl]pyrimidin-4-yl}phenylamino)ethanol |
| "A5" | (S)-3-[{2-Amino-6-[5-(1-methyl-1H-pyrazol-4-yl)-1H-pyrrolo[2,3-b]-pyridin-3-yl]pyrimidin-4-yl}-(4-methoxyphenyl)amino]propane-1,2-diol |
| "A6" | 4-[5-(1-Methyl-1H-pyrazol-4-yl)-1H-pyrrolo[2,3-b]pyridin-3-yl]-6-(1-phenylcyclopentyl)pyrimidin-2-ylamine |
| "A7" | 4-[1-(4-Chlorophenyl)cyclopentyl]-6-[5-(1-methyl-1H-pyrazol-4-yl)-1H-pyrrolo[2,3-b]pyridin-3-yl]pyrimidin-2-ylamine |
| "A8" | N4-(3-Chlorophenyl)-N4-methyl-6-[5-(1-methyl-1H-pyrazol-4-yl)-1H-pyrrolo[2,3-b]pyridin-3-yl]pyrimidine-2,4-diamine |
| "A9" | N4-(2-Fluorophenyl)-N4-methyl-6-[5-(1-methyl-1H-pyrazol-4-yl)-1H-pyrrolo[2,3-b]pyridin-3-yl]pyrimidine-2,4-diamine |
| "A10" | N4-(2-Chlorophenyl)-N4-methyl-6-[5-(1-methyl-1H-pyrazol-4-yl)-1H-pyrrolo[2,3-b]pyridin-3-yl]pyrimidine-2,4-diamine |
| "A11" | N4-Methyl-6-[5-(1-methyl-1H-pyrazol-4-yl)-1H-pyrrolo[2,3-b]-pyridin-3-yl]-N4-phenylpyrimidine-2,4-diamine |

| No. | Structure/name |
|---|---|
| "A12" | N4-Ethyl-6-[5-(1-methyl-1H-pyrazol-4-yl)-1H-pyrrolo[2,3-b]pyridin-3-yl]-N4-phenylpyrimidine-2,4-diamine |
| "A13" | N4-(4-Chlorophenyl)-N4-ethyl-6-[5-(1-methyl-1H-pyrazol-4-yl)-1H-pyrrolo[2,3-b]pyridin-3-yl]pyrimidine-2,4-diamine |
| "A14" | N4-Benzyl-N4-ethyl-6-[5-(1-methyl-1H-pyrazol-4-yl)-1H-pyrrolo[2,3-b]pyridin-3-yl]pyrimidine-2,4-diamine |
| "A15" | 2-[{2-Amino-6-[5-(1-isopropyl-1H-pyrazol-4-yl)-1H-pyrrolo[2,3-b]-pyridin-3-yl]pyrimidin-4-yl}-(2-chlorophenyl)amino]ethanol |
| "A16" | 2-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]ethanol |
| "A17" | 4-(5-Fluoro-2,3-dihydroindol-1-yl)-6-[5-(1-methyl-1H-pyrazol-4-yl)-1H-pyrrolo[2,3-b]pyridin-3-yl]pyrimidin-2-ylamine |
| "A18" | 4-(5-Fluoro-2,3-dihydroindol-1-yl)-6-[5-(1-isopropyl-1H-pyrazol-4-yl)-1H-pyrrolo[2,3-b]pyridin-3-yl]pyrimidin-2-ylamine |
| "A19" | N4-(2-Chlorophenyl)-6-[5-(1-isopropyl-1H-pyrazol-4-yl)-1H-pyrrolo[2,3-b]pyridin-3-yl]-N4-methylpyrimidine-2,4-diamine |

| No. | Structure/name |
|---|---|
| "A20" | N4-Ethyl-6-[5-(1-methyl-1H-pyrazol-4-yl)-1H-pyrrolo[2,3-b]pyridin-3-yl]-N4-1,3,4-thiadiazol-2-ylpyrimidine-2,4-diamine |
| "A21" | 1-({2-Amino-6-[5-(1-methyl-1H-pyrazol-4-yl)-1H-pyrrolo[2,3-b]-pyridin-3-yl]pyrimidin-4-yl}phenylamino)-3-methoxypropan-2-ol |
| "A22" | 3-[{2-Amino-6-[5-(1-methyl-1H-pyrazol-4-yl)-1H-pyrrolo[2,3-b]-pyridin-3-yl]pyrimidin-4-yl}-(2,3-dihydroxypropyl)amino]benzonitrile |
| "A23" | 3-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]propionic acid |
| "A24" | Methyl [{2-amino-6-[5-(1-methyl-1H-pyrazol-4-yl)-1H-pyrrolo[2,3-b]pyridin-3-yl]pyrimidin-4-yl}-(4-chlorophenyl)amino]-acetate |
| "A25" | 2-[{2-Amino-6-[5-(1-methyl-1H-pyrazol-4-yl)-1H-pyrrolo[2,3-b]-pyridin-3-yl]pyrimidin-4-yl}-(2,4-difluorophenyl)amino]ethanol |
| "A26" | 2-[{2-Amino-6-[5-(1-methyl-1H-pyrazol-4-yl)-1H-pyrrolo[2,3-b]-pyridin-3-yl]pyrimidin-4-yl}-(2-fluorophenyl)amino]ethanol |

| No. | Structure/name |
|---|---|
| "A27" | 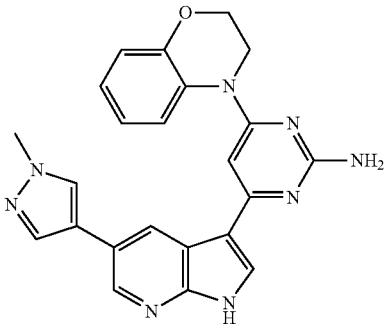 4-(2,3-Dihydrobenzo-1,4-oxazin-4-yl)-6-[5-(1-methyl-1H-pyrazol-4-yl)-1H-pyrrolo[2,3-b]pyridin-3-yl]pyrimidin-2-ylamine |
| "A28" | N4-(3-Fluorophenyl)-6-[5-(1-methyl-1H-pyrazol-4-yl)-1H-pyrrolo[2,3-b]pyridin-3-yl]-N4-(2-morpholin-4-ylethyl)pyrimidine-2,4-diamine |
| "A29" | N4-(2-Chlorophenyl)-N4-(2-methoxyethyl)-6-[5-(1-methyl-1H-pyrazol-4-yl)-1H-pyrrolo[2,3-b]pyridin-3-yl]pyrimidine-2,4-diamine |

| No. | Structure/name |
|---|---|
| "A30" | 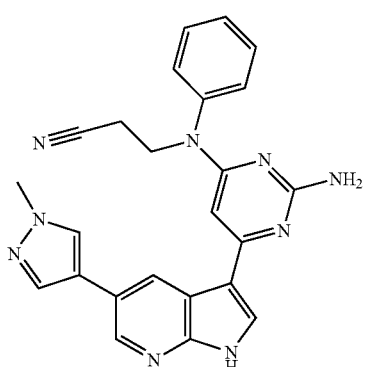 3-({2-Amino-6-[5-(1-methyl-1H-pyrazol-4-yl)-1H-pyrrolo[2,3-b]-pyridin-3-yl]pyrimidin-4-yl}phenylamino)propionitrile |
| "A30a" | (3-Fluorophenyl)methyl-{6-[5-(1-methyl-1H-pyrazol-4-yl)-1H-pyrrolo[2,3-b]pyridin-3-yl]pyrimidin-4-yl}amine |
| "A31" | N4-(3-Aminopropyl)-6-[5-(1-methyl-1H-pyrazol-4-yl)-1H-pyrrolo[2,3-b]pyridin-3-yl]-N4-phenylpyrimidine-2,4-diamine |

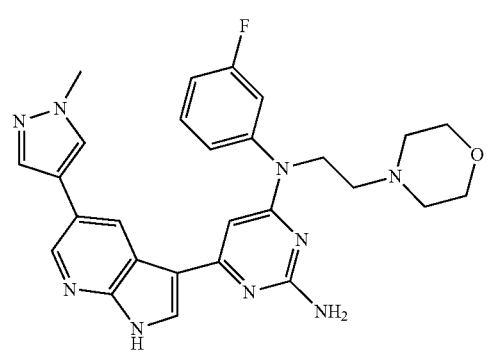

| No. | Structure/name | No. | Structure/name |
|---|---|---|---|
| "A32" | 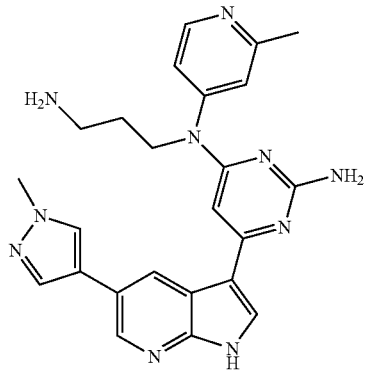 N4-(3-Aminopropyl)-6-[5-(1-methyl-1H-pyrazol-4-yl)-1H-pyrrolo[2,3-b]pyridin-3-yl]-N4-(2-methylpyridin-4-yl)pyrimidine-2,4-diamine | "A35" | 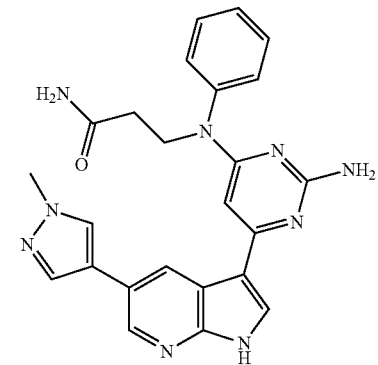 3-({2-Amino-6-[5-(1-methyl-1H-pyrazol-4-yl)-1H-pyrrolo[2,3-b]-pyridin-3-yl]pyrimidin-4-yl}phenylamino)propionamide |
| "A33" | 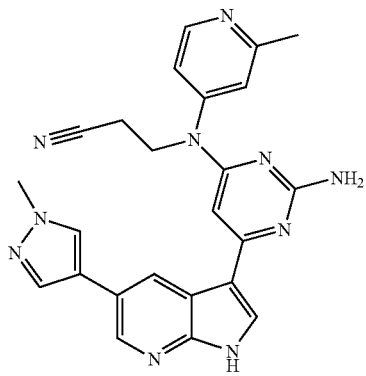 3-[{2-Amino-6-[5-(1-methyl-1H-pyrazol-4-yl)-1H-pyrrolo[2,3-b]-pyridin-3-yl]pyrimidin-4-yl}-(2-methylpyridin-4-yl)amino]-propionitrile | "A36" | 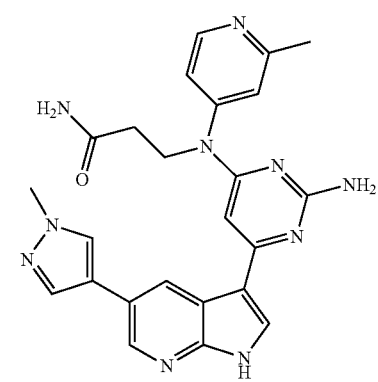 3-[{2-Amino-6-[5-(1-methyl-1H-pyrazol-4-yl)-1H-pyrrolo[2,3-b]-pyridin-3-yl]pyrimidin-4-yl}-(2-methylpyridin-4-yl)amino]-propionamide |
| "A34" | 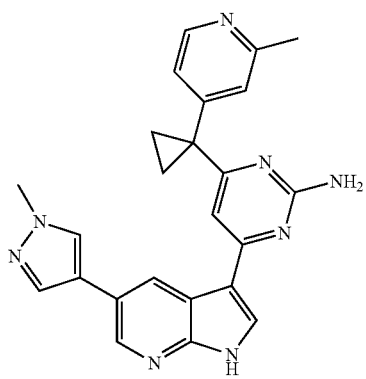 4-[5-(1-Methyl-1H-pyrazol-4-yl)-1H-pyrrolo[2,3-b]pyridin-3-yl]-6-[1-(2-methylpyridin-4-yl)cyclopropyl]pyrimidin-2-ylamine | "A37" | 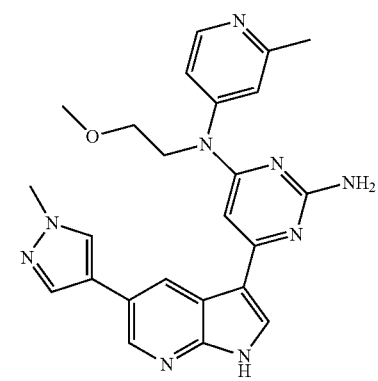 N4-(2-Methoxyethyl)-6-[5-(1-methyl-1H-pyrazol-4-yl)-1H-pyrrolo[2,3-b]pyridin-3-yl]-N4-(2-methylpyridin-4-yl)pyrimidine-2,4-diamine |

| No. | Structure/name |
|---|---|
| "A38" | 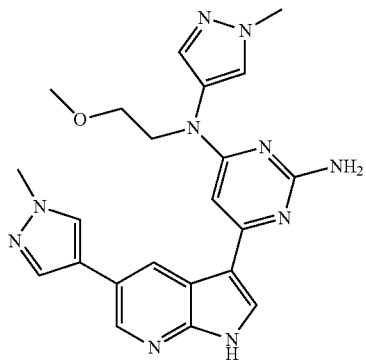<br>N4-(2-Methoxyethyl)-6-[5-(1-methyl-1H-pyrazol-4-yl)-1H-pyrrolo[2,3-b]pyridin-3-yl]-N4-(1-methylpyrazol-4-yl)pyrimidine-2,4-diamine |
| "A39" | 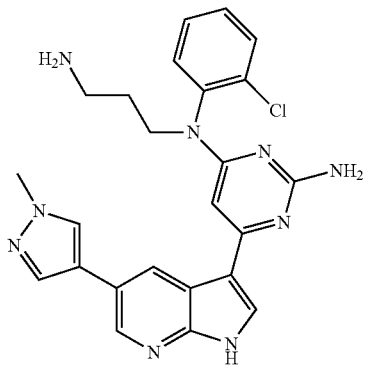<br>N4-(3-Aminopropyl)-6-[5-(1-methyl-1H-pyrazol-4-yl)-1H-pyrrolo[2,3-b]pyridin-3-yl]-N4-(2-chlorophenyl)pyrimidine-2,4-diamine |
| "A40" | 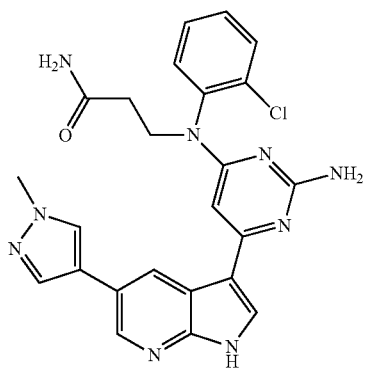<br>3-[{2-Amino-6-[5-(1-methyl-1H-pyrazol-4-yl)-1H-pyrrolo[2,3-b]-pyridin-3-yl]pyrimidin-4-yl}-(2-chlorophenyl)amino]propionamide |

| No. | Structure/name |
|---|---|
| "A41" | 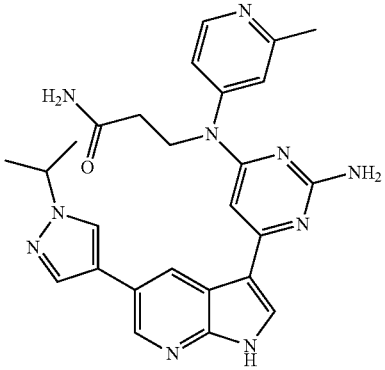<br>3-[{2-Amino-6-[5-(1-isopropyl-1H-pyrazol-4-yl)-1H-pyrrolo[2,3-b]-pyridin-3-yl]pyrimidin-4-yl}-(2-methylpyridin-4-yl)amino]-propionamide |
| "A42" | 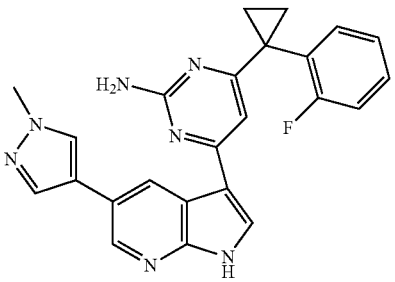<br>4-[1-(2-Fluorophenyl)cyclopropyl]-6-[5-(1-methyl-1H-pyrazol-4-yl)-1H-pyrrolo[2,3-b]pyridin-3-yl]pyrimidin-2-ylamine |
| "A43" | 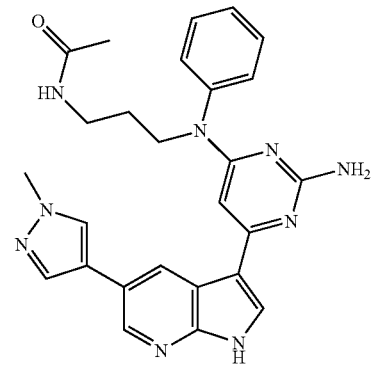<br>N-[3-({2-Amino-6-[5-(1-methyl-1H-pyrazol-4-yl)-1H-pyrrolo[2,3-b]-pyridin-3-yl]pyrimidin-4-yl}phenylamino)propyl]acetamide | or a pharmaceutically acceptable salt, tautomer or stereoisomer thereof.

2. A method according to claim 1, where the tumour originates from a tumour of the squamous epithelium, of the bladder, of the kidneys, of the head and neck, of the oesophagus, of the cervix, of the thyroid, of the intestine, of the liver, of the brain, of the prostate, of the urogenital tract, of the lymphatic system, of the stomach, of the larynx or of the lung.

3. A method according to claim 1, where the tumour originates from monocytic leukaemia, lung adenocarcinoma, small-cell lung carcinoma, pancreatic cancer, colon carcinoma, glioblastoma or breast carcinoma.

4. A method according to claim 1, further comprising administering a compound selected from the group consisting of an 1) oestrogen receptor modulator, 2) androgen receptor modulator, 3) retinoid receptor modu-lator, 4) cytotoxic agent, 5) antiproliferative agent, 6) prenyl-protein transferase inhibitor, 7) HMG-CoA reductase inhibitor, 8) HIV protease inhibitor, 9) reverse transcriptase inhibitor and 10) angiogenesis inhibitors.

5. A method according to claim 4, further comprising administering radiotherapy.

6. A method according to claim 1, wherein the compound A1 or a pharmaceutically acceptable salt thereof is administered.

7. A method according to claim 1, wherein one of the compounds A2 to A11 or a pharmaceutically acceptable salt thereof is administered.

8. A method according to claim 1, wherein one of the compounds A12 to A22 or a pharmaceutically acceptable salt thereof is administered.

9. A method according to claim 1, wherein one of the compounds A23 to A32 or a pharmaceutically acceptable salt thereof is administered.

10. A method according to claim 1, wherein one of the compounds A33 to A43 or a pharmaceutically acceptable salt thereof is administered.

11. A method according to claim 1, wherein the tumour originates from a tumour of the squamous epithelium.

12. A method according to claim 1, wherein the tumour originates from a tumour of the bladder, of the prostate or of the kidneys.

13. A method according to claim 1, wherein the tumour originates from a tumour of the stomach, of the intestine or of the oesophagus or originates from colon carcinoma.

14. A method according to claim 1, wherein the tumour originates from a tumour of the head and neck.

15. A method according to claim 1, wherein the tumour originates from a tumour of the cervix or of the urogenital tract.

16. A method according to claim 1, wherein the tumour originates from a tumour of the thyroid, of the lymphatic system or of the larynx or originates from pancreatic cancer.

17. A method according to claim 1, wherein the tumour originates from a tumour of the liver or originates from monocytic leukaemia.

18. A method according to claim 1, wherein the tumour originates from a tumour of the brain or originates from glioblastoma.

19. A method according to claim 1, wherein the tumour originates from breast carcinoma.

20. A method according to claim 1, wherein the tumour originates from a tumour of the lung or originates from lung adenocarcinoma, small-cell lung carcinoma.

* * * * *

SEQUENCE LISTING

```
<160> NUMBER OF SEQ ID NOS: 3

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-dimethyl-L-valyl
<220> FEATURE:
<221> NAME/KEY: MOD_RES
<222> LOCATION: (2)..(2)
<223> OTHER INFORMATION: L-valyl
<220> FEATURE:
<221> NAME/KEY: MOD_RES
<222> LOCATION: (3)..(3)
<223> OTHER INFORMATION: N-methyl-L-valyl
<220> FEATURE:
<221> NAME/KEY: MOD_RES
<222> LOCATION: (4)..(4)
<223> OTHER INFORMATION: L-prolyl
<220> FEATURE:
<223> OTHER INFORMATION: C-term t-butylamide

<400> SEQUENCE: 1

Val Val Val Pro Pro
1               5
```

```
<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5

<210> SEQ ID NO 3
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term biotin
<220> FEATURE:
<221> NAME/KEY: MOD_RES
<222> LOCATION: (1)..(2)
<223> OTHER INFORMATION: bAla

<400> SEQUENCE: 3

Ala Ala Lys Thr Phe Cys Gly Thr Pro Glu Tyr Leu Ala Pro Glu Val
1               5                   10                  15

Arg Arg Glu Pro Arg Ile Leu Ser Glu Glu Glu Gln Glu Met Phe Arg
                20                  25                  30

Asp Phe Asp Tyr Ile Ala Asp Trp Cys
                35                  40
```